US012653849B2

(12) United States Patent　　　(10) Patent No.:　US 12,653,849 B2

Monsul et al.　　　　　　　　　　　 (45) **Date of Patent:　*Jun. 16, 2026**

(54) MATERIALS AND METHODS FOR INHIBITING A VIRAL INFECTION, INCLUDING A CORONAVIRUS INFECTION

(71) Applicant: Quorum Innovations, Inc., Sarasota, FL (US)

(72) Inventors: Nicholas T. Monsul, Sarasota, FL (US); Eva A. Berkes, Sarasota, FL (US); Frederick T. Boehm, Sarasota, FL (US); Yu-Hsien Liao, Sarasota, FL (US)

(73) Assignee: QUORUM INNOVATIONS, INC., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/493,979

(22) Filed: Oct. 25, 2023

(65) Prior Publication Data

US 2024/0075083 A1　　Mar. 7, 2024

Related U.S. Application Data

(63) Continuation of application No. 17/418,440, filed as application No. PCT/US2021/036104 on Jun. 7, 2021, now Pat. No. 11,826,390.

(Continued)

(51) Int. Cl.
*A61K 35/74*　　　(2015.01)
*A61K 35/68*　　　(2006.01)
(Continued)

(52) U.S. Cl.
CPC .......... *A61K 35/747* (2013.01); *A61K 38/164* (2013.01); *A61K 45/06* (2013.01);
(Continued)

(58) Field of Classification Search
CPC .................................................... A61K 35/747
See application file for complete search history.

(56) References Cited

U.S. PATENT DOCUMENTS 10,617,726 B2 *　4/2020　Berkes ..................... A61P 37/08
2017/0020139 A1 *　1/2017　Berkes ..................... A61P 37/08

FOREIGN PATENT DOCUMENTS

CN　　　1701116 A　　11/2005
CN　　108135947 A　　6/2018
(Continued)

OTHER PUBLICATIONS

"Hypothetical protein [*Limosilactobacillus fermentum*]", NCBI Genbank accession No. WP_003682205, 2016, (https://www.ncbi.nlm.nih.gov/protein/WP_003682205.1?report=genbank&log$=prot . . . , accessed on Sep. 9, 2021).

(Continued)

*Primary Examiner* — Gary Benzion

(74) *Attorney, Agent, or Firm* — SALIWANCHIK, LLOYD & EISENSCHENK

(57) ABSTRACT

The subject invention provides compositions and methods for inhibiting viral infections. Preferred embodiments of the invention provide pharmaceutical compositions, and the methods of using the same, comprising a strain of *Lactobacillus fermentum* bacterium, or bioactive extracts thereof.

13 Claims, 12 Drawing Sheets

Specification includes a Sequence Listing.

After 60 Hours Coincubation

Normal ST cell (AB2)　　　　ST cell / 5%Qi601S(CB3)

ST cell / PRCV(AB11)　　　ST/PRCV/5%Qi601S(CB11)

Related U.S. Application Data

(60) Provisional application No. 63/035,733, filed on Jun. 6, 2020.

(51) Int. Cl.

| | |
|---|---|
| *A61K 35/747* | (2015.01) |
| *A61K 38/16* | (2006.01) |
| *A61K 45/06* | (2006.01) |
| *A61P 31/14* | (2006.01) |
| *C07K 14/335* | (2006.01) |
| *C12N 1/205* | (2026.01) |
| *C12R 1/225* | (2006.01) |

(52) U.S. Cl.

CPC ............ *A61P 31/14* (2018.01); *C07K 14/335* (2013.01); *C12N 1/205* (2021.05); *C12R 2001/225* (2021.05)

(56) References Cited

FOREIGN PATENT DOCUMENTS

| WO | 2007040445 | A1 | 4/2007 |
|---|---|---|---|
| WO | 2012141540 | A2 | 10/2012 |
| WO | 2017015275 | A1 | 1/2017 |
| WO | 2017210553 | A1 | 12/2017 |
| WO | 2010027344 | A1 | 3/2019 |
| WO | 2021226318 | A1 | 11/2021 |

OTHER PUBLICATIONS

Subhadra, B., et al., "Draft Whole-Genome Sequence of Lactobacillus fermentum LfQi6, Derived from the Human Microbiome." Genome Announcements, 2015, 3(3): e00423-15, pp. 1-2.

* cited by examiner

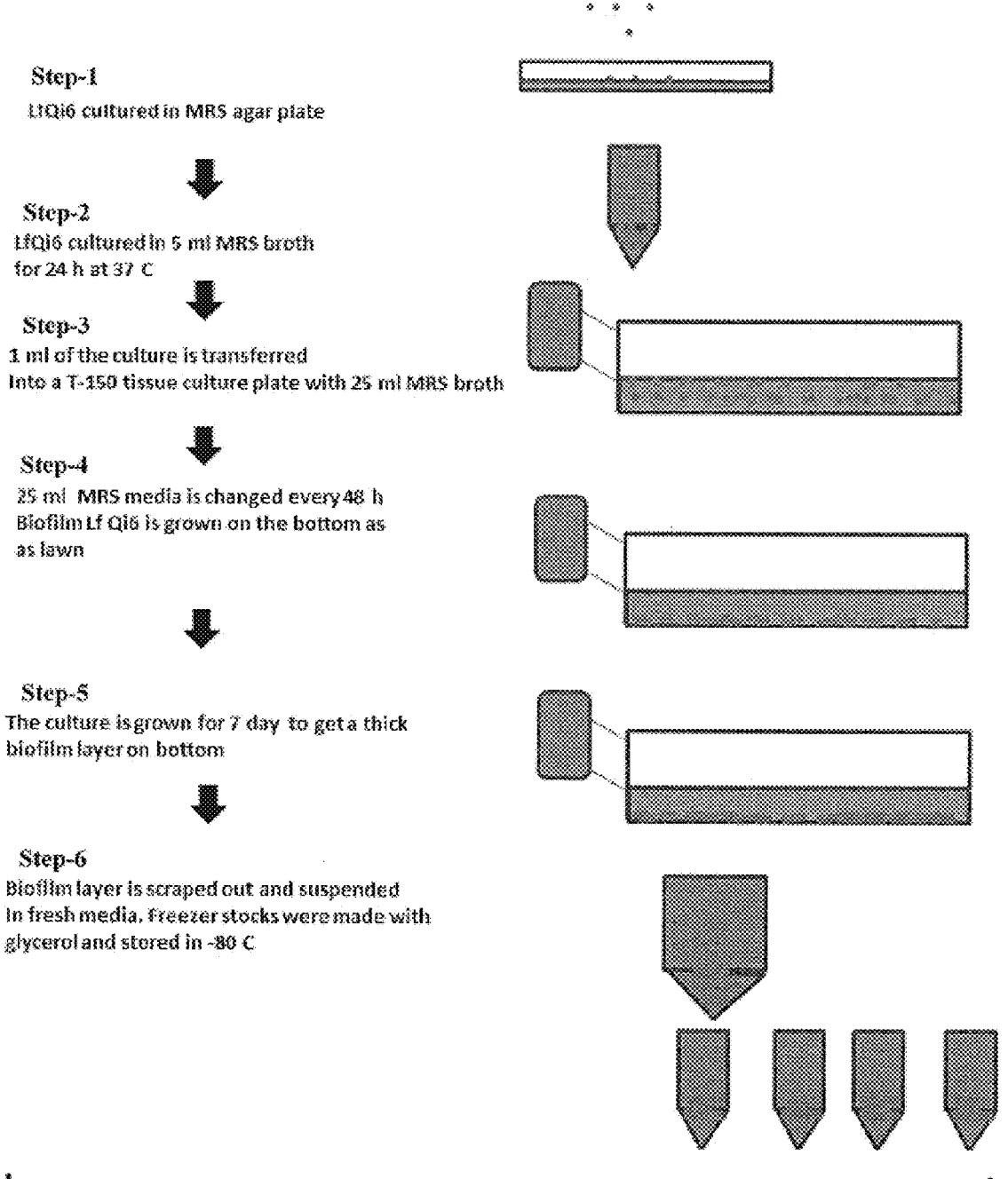

Step-1
LfQi6 cultured in MRS agar plate

Step-2
LfQi6 cultured in 5 ml MRS broth
for 24 h at 37 C

Step-3
1 ml of the culture is transferred
into a T-150 tissue culture plate with 25 ml MRS broth

Step-4
25 ml MRS media is changed every 48 h
Biofilm Lf Qi6 is grown on the bottom as
as lawn

Step-5
The culture is grown for 7 day to get a thick
biofilm layer on bottom

Step-6
Biofilm layer is scraped out and suspended
in fresh media. Freezer stocks were made with
glycerol and stored in -80 C

FIG. 1

Step-1
Biofilm phenotype LfQi6
in frozen stock is cultured in
10 ml fresh MRS media for 24h
at 37C

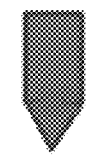

Step-2
Inoculate 10 ml culture into 25 L
MRS media with 500 g sterile glass
wool

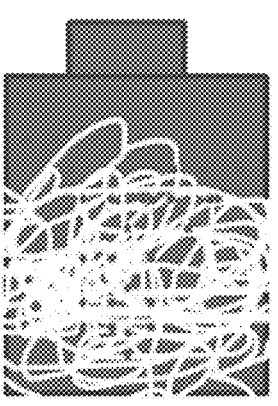

Step-3
Culture it for 72 g in
static conditions at 37C
Mix the culture every 24h
with a gentle shaking

Step-4
Harvest the media and glass
Wool. Sonicate the glass wool
to detach biofilm cells .

Step-5
Centrifuge the cells to concentrate
the biofilm LfQi6. Suspend in sterile
Water
Yied: 50g/25 Liter culture

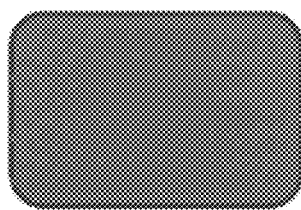

FIG. 2

Step-1
50g Biofilm phenotype LfQi6
Is suspended in 1 liter sterile
Water. Gentle mixed for 24 hr
at room temperature to

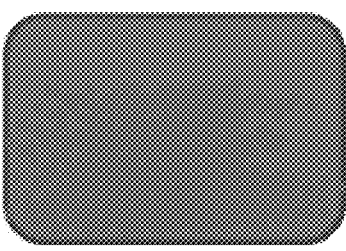

Step-2
Gentle mixer for 24 hr
at room temperature for
passive release of multiple
bioactives

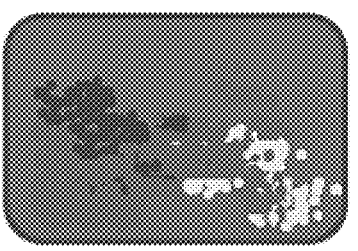

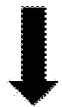

Step-3
The mixture is then sonicated
for 30 min (50 KHz, 200 watt) using
OmniSonic Ruptor 400 in into niform
lysate

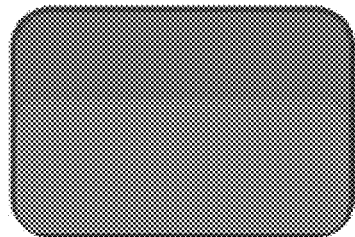

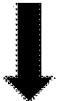

Step-4
The sonicated lysate is frozen

Step-5
The frozen lysate
Is lyophilized into a fine
powder

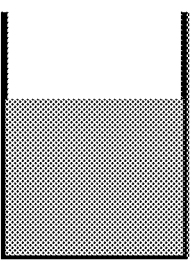

FIG. 4

1: *E. coli* BL21 Empty Vector     7: *E. coli* BL21 clone#6
2: *E. coli* BL21 clone#1     8: *E. coli* BL21 clone#7
3: *E. coli* BL21 clone#2     9: *E. coli* BL21 clone#8
4: *E. coli* BL21 clone#3     10: *E. coli* BL21 clone#9
5: *E. coli* BL21 clone#4     11: *E. coli* BL21 clone#10
6: *E. coli* BL21 clone#5

After 60 Hours Coincubation

Plate A

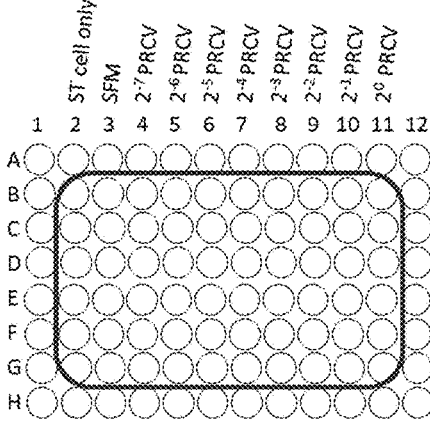

Only use center wells for the Test

Plate A: (No Protection Control)
A. Virus particles only (Serial Dilution)

1. Seed Cell 80-90% confluent
2. Add Serum Free Medium (SFM) 100uL
3. Add PRCV 100uL (Serial Dilution)
4. Incubate 4 days
5. MTT Assay After 60 Hours                    Red Arrow: CPE (Cytopathic Effect)

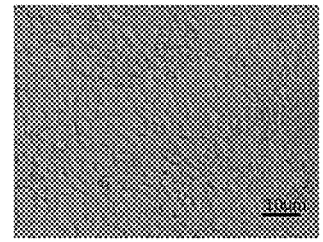

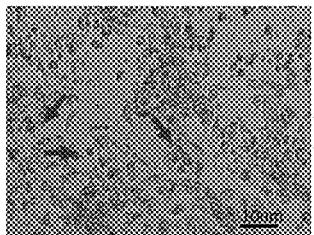

ST cell (AB2)                    ST cell / PRCV (AB11)

FIG. 11

After 60 Hours Coincubation

Plate B

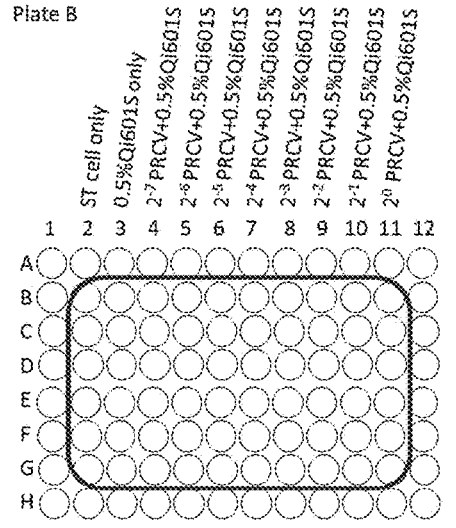

Only use center wells for the Test

Second Plate (0.5% Qi601S Protection)
B. 0.5% Qi601S + Virus particles (Serial Dilution)

1. Seed Cell 80-90% confluent
2. Add 0.5% Qi601S 100uL
3. Add PRCV 100uL (Serial Dilution)
4. Incubate 4 Days
5. MTT Assay After 60 Hours                    Red Arrow: CPE (Cytopathic Effect)

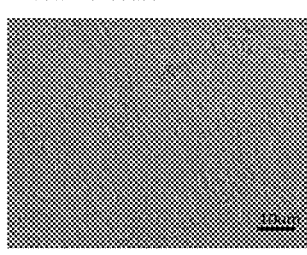

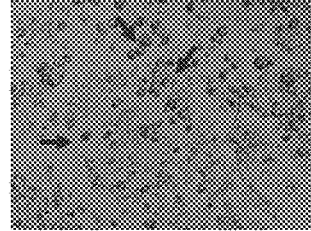

ST cell (BB2)                    ST/PRCV/0.5%Qi601S (BB11)

FIG. 12

After 60 Hours Coincubation
Plate C
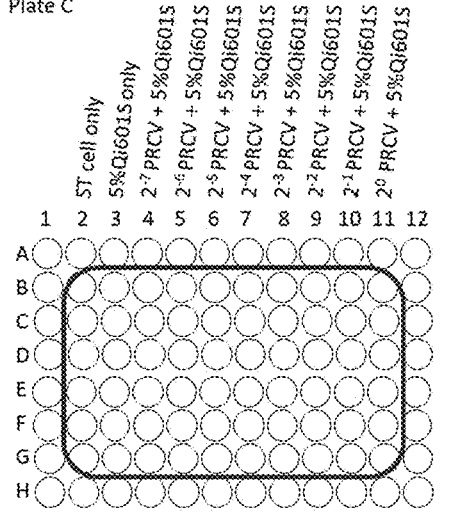
Only use center wells for the Test
Plate C : (5% Qi601S Protection)
C. 5% Qi601S + Virus particles (Serial Dilution)
1. Seed Cell 80-90% confluent
2. Add 5% Qi601S 100uL
3. Add PRCV 100uL (Serial Dilution)
4. Incubate 4 Days
5. MTT Assay
After 60 Hours
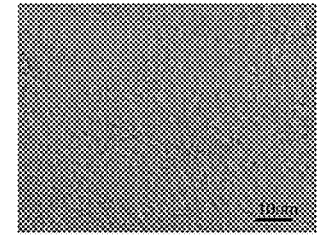
ST cell (CB2)                ST cell / PRCV/ 5% Qi601S (CB11)
FIG. 13
After 60 Hours Coincubation
Plate B
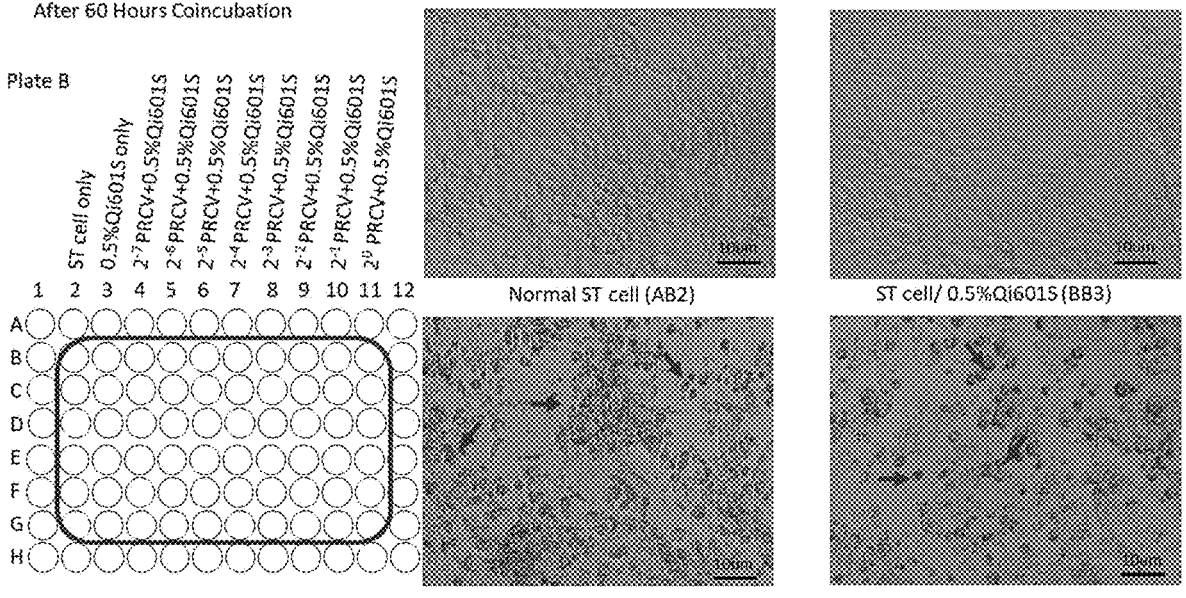
Normal ST cell (AB2)                ST cell/ 0.5%Qi601S (BB3)
ST cell / PRCV (AB11)                ST/PRCV/0.5%Qi601S (BB11)
FIG. 14

MATERIALS AND METHODS FOR INHIBITING A VIRAL INFECTION, INCLUDING A CORONAVIRUS INFECTION

CROSS-REFERENCE TO RELATED APPLICATIONS

This application is a continuation of U.S. patent application Ser. No. 17/418,440, filed Jun. 25, 2021; which is a National Stage Application of International Application No. PCT/US2021/036104, filed Jun. 7, 2021; which claims priority to U.S. Provisional Patent Application Ser. No. 63/035,733, filed Jun. 6, 2020; all of which are incorporated herein by reference in their entirety.

SEQUENCE LISTING

The Sequence Listing for this application is labeled "SeqList-05Jun20-ST25.txt," which was created on Jun. 5, 2020, and is 3 KB. The Sequence Listing is incorporated herein by reference in its entirety.

BACKGROUND OF THE INVENTION

Beginning in the 1960s, a variety of human-infecting coronaviruses have been identified. From the family Coronaviridae, these viruses primarily infect the upper respiratory and gastrointestinal tracts. Whilst many such infections are mild and routinely include the common cold, for example, far more pathogenic and potentially lethal strains exist, including SARS, MERS, and the 2019 outbreak strain of SARS-CoV-2, (2019-nCov or COVID-19).

SARS (Severe Acute Respiratory Syndrome), MERS (Middle East Respiratory Syndrome) and SARS-CoV-2 (SARS-related Coronavirus 2) are all highly pathogenic human coronaviruses responsible for acute and chronic diseases of the respiratory, hepatic, gastrointestinal and neurological systems. It is thought that each virus emerged from animal reservoirs and transferred to humans, thereby resulting in human epidemics, with the outbreak of SARS in 2002, MERS in 2012, and SARS-CoV-2 in late 2019.

Coronaviruses are enveloped single-stranded RNA viruses named so for their crown-like surface structure composed of spike (S), envelope (E), membrane (M) and nucleocapsid (N) proteins. The spike protein in particular is responsible for the action of entering a host cell, wherein the coronavirus is able to transcribe its RNA for intracytoplasmic replication. Indeed, coronaviruses have a unique ability to replicate and survive in the intracellular space of a macrophage, whereby multiple encoded interferon antagonists are thought to hinder the activation of type I interferon (IFN) and interferon stimulated genes (ISGs), dampening the host immune response and contributing to the resultant pathogenesis of the virus (Rose et al. 2010, Journal of Virology 84 (11): 5656-5669).

Upon genome replication and polyprotein formation, the viruses assemble and are released from the infected cell to further disseminate. Transmission between hosts is considered to occur primarily by contact with respiratory droplets infected with such viral particles, generated through sneezing and coughing (CDC.gov, 2020).

Coronaviruses can emerge from animal reservoirs to cause significant epidemics in humans, as exemplified by Severe Acute Respiratory Syndrome coronavirus (SARS-CoV) in 2002-2003 and Middle East Respiratory Syndrome coronavirus (MERS-CoV), which was recognized as an emerging virus in 2012, each of which resulted in over 8000 infections and 774 deaths, and 2500 infections and 862 deaths, per respective outbreak (WHO, 2020). Declared a global emergency by the World Health Organisation (WHO), the newly discovered and rapidly disseminating SARS-CoV-2, sharing ~70% genetic similarity to the SARS-CoV, is likely to have similar epidemiological characteristics and thus presents a pressing area of healthcare concern. Crucially, there are no vaccines or antiviral drugs suitable for the prevention or treatment of human coronavirus infections at this time (Habibzadeh & Stoneman 2020, Int J Occup Environ Med 11 (2): 65-71).

A SARS-CoV-2 health emergency evidences a lack of effective virus-specific treatments or vaccines, which thus leads to a high unmet need for the protection of high-risk populations, including the elderly, health care workers and patients in acute danger of nosocomial transmission of SARS-CoV-2, or in other confined spaces, such as during quarantine settings.

Without any such viable antiviral or vaccine currently approved, there exists a particular need for a safe and effective method of treating or preventing infections or symptoms thereof caused by a coronavirus, in particular those related to SARS-CoV-2.

Biofilms are initiated when free-floating, planktonic bacteria anchor to a biologic or inert surface such as an indwelling medical device. The attached bacteria multiply and progress from a state of monolayer to a microcolony and then to a critical mass, at which point bacterial crosstalk occurs, triggering a phenomenon known as quorum sensing that leads to the biofilm phenotype. Quorum sensing can turn on biofilm-producing genes that are not expressed in planktonic bacteria. The bacteria respond collectively to express factors that are specific to the biofilm phenotype, which leads to the secretion of an exopolysaccharide (EPS) matrix, definitive of the biofilm phenotype.

The biofilm phenotype is characterized morphologically by the formation of microbial towers, which are composed of layers of embedded, live bacteria with intervening water channels. Under the right environmental conditions, free-floating bacteria are released from the biofilms, and the cycle is continued at other surfaces.

SUMMARY OF THE INVENTION

The subject invention provides compositions and methods for inhibiting viral infections, including coronavirus infections. Preferred embodiments of the invention provide pharmaceutical compositions, and methods of using the same. In preferred embodiments, the compositions of the subject invention inhibit viral entry into cells and/or viral spread between cells via immunomodulation of the innate immune system.

Advantageously, preferred compositions and treatment methods provided herein are effective in inhibiting viral infections, including by, in some embodiments, inducing protective innate immunity. The viral inhibitory activity may also be achieved, in some embodiments, via binding of a component of the composition to the ACE2 receptor, thereby blocking entry of the virus into a cell.

In certain embodiments, the compositions of the subject invention can be used effectively in the treatment of acute and chronic viral infections. In specific embodiments, the subject is infected, or at risk for infection, with a coronavirus. Such coronaviruses include, for example, Severe Acute Respiratory Syndrome associated Coronavirus (SARS- CoV), Middle East Respiratory Syndrome associated Coronavirus (MERS-CoV), and the SARS-CoV-2 virus discovered in late 2019.

In one aspect, the subject invention provides therapeutic compositions for treating a viral infection, comprising a bacterial strain, or a bioactive extract therefrom, and a pharmaceutically acceptable excipient. In other embodiments, the subject invention provides prophylactic compositions for preventing the onset or spread of a viral infection.

In certain embodiments, the compositions comprise a strain of *Lactobacillus fermentum* bacterium, or a bioactive extract thereof. In preferred embodiments, extracts of the bacteria are obtained when the bacteria are grown as biofilm. The subject invention also provides compositions comprising *L. fermentum* bacterium, or bioactive extracts thereof, in a lyophilized, freeze dried, and/or lysate form.

In some embodiments, the bacterial strain is *Lactobacillus fermentum* Qi6, also referred to herein as LfQi6. In one embodiment, the subject invention provides an isolated or a biologically pure culture of LfQi6. In another embodiment, the subject invention provides a biologically pure culture of LfQi6, grown as a biofilm. Specifically taught herein are methods for inducing and identifying the biofilm phenotype. Further provided herein are methods of utilizing the biofilm phenotype, as well as extracts of the biofilm phenotype, and lysates thereof. In preferred embodiments, the pharmaceutical compositions comprise bioactive extracts of LfQi6 biofilm. In one embodiment, the extract has been given the designation Qi601S.

In further embodiments, the present invention provides anti-viral proteins. In a specific embodiment, the present invention provides "Qi611S," a protein having an amino acid sequence according to SEQ ID NO. 1. In certain embodiments, the present invention also provides "Qi611S Proteins," which include Qi611S, as well as biologically-active fragments and variants thereof.

In some embodiments, Qi611S Proteins can be produced by a cell, preferably a bacterial cell. Thus, in specific embodiments, the present invention provides methods for producing a Qi611S Protein, the methods comprise cultivating a cell having a nucleotide sequence that encodes all or a portion of SEQ ID NO. 1, or a variant or fragment thereof, under conditions favorable for expression of the protein. In preferred embodiments, the nucleotide sequence is Qi611s (SEQ ID NO. 2). Optionally, the protein can be purified from the culture.

In one embodiment, the methods utilize a microorganism, e.g., *Lactobacillus fermentum* Qi6, having the Qi611s nucleotide sequence (SEQ ID NO. 2). Qi611s encodes the amino acid sequence according to SEQ ID NO. 1 (Qi611S).

In another embodiment, the cell is a microorganism that has been recombinantly altered to possess the ability to express a Qi611S Protein. In a specific embodiment, the microbe possesses all, or a portion, of the Qi611s gene. Thus, in certain embodiments, the present invention provides a recombinant cell possessing all or a portion of the DNA sequence according to SEQ ID NO. 2, and/or that is capable of expressing a protein having an amino acid sequence according to SEQ ID NO. 1, or a fragment or variant of SEQ ID NO. 1. In an exemplary embodiment, the recombinant cell is *E. coli* BL21 or *E. coli* C43.

Such transformation of cells can be accomplished using techniques well known to those skilled in the microbiological arts. In one embodiment, the nucleotide sequence can be modified to optimize expression of a Qi611S Protein.

In preferred embodiments, the present invention provides compositions comprising a Qi611S Protein and/or a cell comprising all or a portion of a DNA sequence according to SEQ ID NO. 2, and, optionally, a pharmaceutically acceptable carrier.

Pharmaceutically acceptable carriers can comprise substances used for administrating the composition to a subject according to a specific route, including, for example, oral administration, inhalation, eye drops, injection (e.g., subcutaneous, intravenous, intramuscular, intraperitoneal, intrathecal, and/or subdermal), and/or topical administration (e.g., via dermal absorption). In certain embodiments, the composition can be formulated as a food item, capsule, pill, drinkable liquid, lotion, cream, emulsion, ointment, oil, gel, serum, aerosol, mist, vapor, and/or combinations thereof.

In some embodiments, the protein can be extracted and, optionally, purified from a cell culture before being formulated into the composition. In some embodiments, the composition comprises a cell capable of producing a Qi611S Protein. In one embodiment, the cell is in a lyophilized, freeze dried, and/or lysate form. In one embodiment, the composition comprises a cell culture in a biofilm state.

In another aspect, the subject invention provides a method of inhibiting a viral infection, comprising administering to a subject an effective amount of the composition, wherein the composition preferably comprises one or more bioactive extracts of the LfQi6 biofilm.

In one embodiment the subject invention provides a self-decontaminating surface wherein a protein or cell of the subject invention has been applied to the surface. The protein can be, for example, a Qi611S protein. Preferably, the surface has antiviral properties. The surface can be, for example, cloth, textile, metal, ceramic, wood, skin, liquid, plastic or glass.

BRIEF DESCRIPTION OF THE FIGURES

FIG. 1 shows a Lf Qi6 Culture procedure. Step 1: Lf Qi6 cultured in MRS agar plate; Step 2: Lf Qi6 cultured in 5 ml MRS broth for 24 hour at 37° C.; Step 3: 0.1 ml of the culture is transferred into a T-150 tissue culture plate with 25 ml MRS broth; Step 4: 25 ml MRS media is changed every 48 hours, biofilm Lf Qi6 is grown on the bottom as lawn; Step 5: the culture is grown for 7 days to get a thick biofilm layer on bottom; Step 6: Biofilm layer is scraped out and suspended in fresh medium. Freezer stocks can be made with glycerol and stored in −80°.

FIG. 2 illustrates a Lf Qi6 Scale-up Culture Procedure. Step 1: Biofilm phenotype Lf Qi6 is cultured in 10 ml fresh MRS medium for 24 hour at 37°; Step 2: Inoculate 10 ml culture into 25 L MRS medium with 500 g sterile glass wool; Step 3: Culture it for 72 hours in static conditions at 37° C. Mix the culture every 24 hours with a gentle shaking; Step 4: Harvest the medium and glass wool. Sonicate the glass wool to detach biofilm cells; Step 5: Centrifuge the cells to concentrate the biofilm Lf Qi6. Suspend in sterile water.

FIG. 4 illustrates an example of Lf Qi6 downstream processing. Step 1: 50 g biofilm phenotype Lf Qi6 is suspended in 1 L of sterile water; Step 2: The suspension is gently mixed for 24 hours at room temperature for passive release of bioactive substances; Step 3: the mixture is then sonicated for 30 minutes (50 KHz, 200 watt) into a uniform lysate using an Omni Sonic Ruptor 400; Step 4: the sonicated lysate is frozen; Step 5: the frozen lysate is lyophilized into a fine powder.

FIGS. 11-15 show control of PRCB by a composition of the subject invention at various concentrations. Essentially complete inhibition with no cytotoxicity is achieved after 60 hours. Similar results were achieved after 24 hours.

BRIEF DESCRIPTION OF THE SEQUENCES

Figure 3:
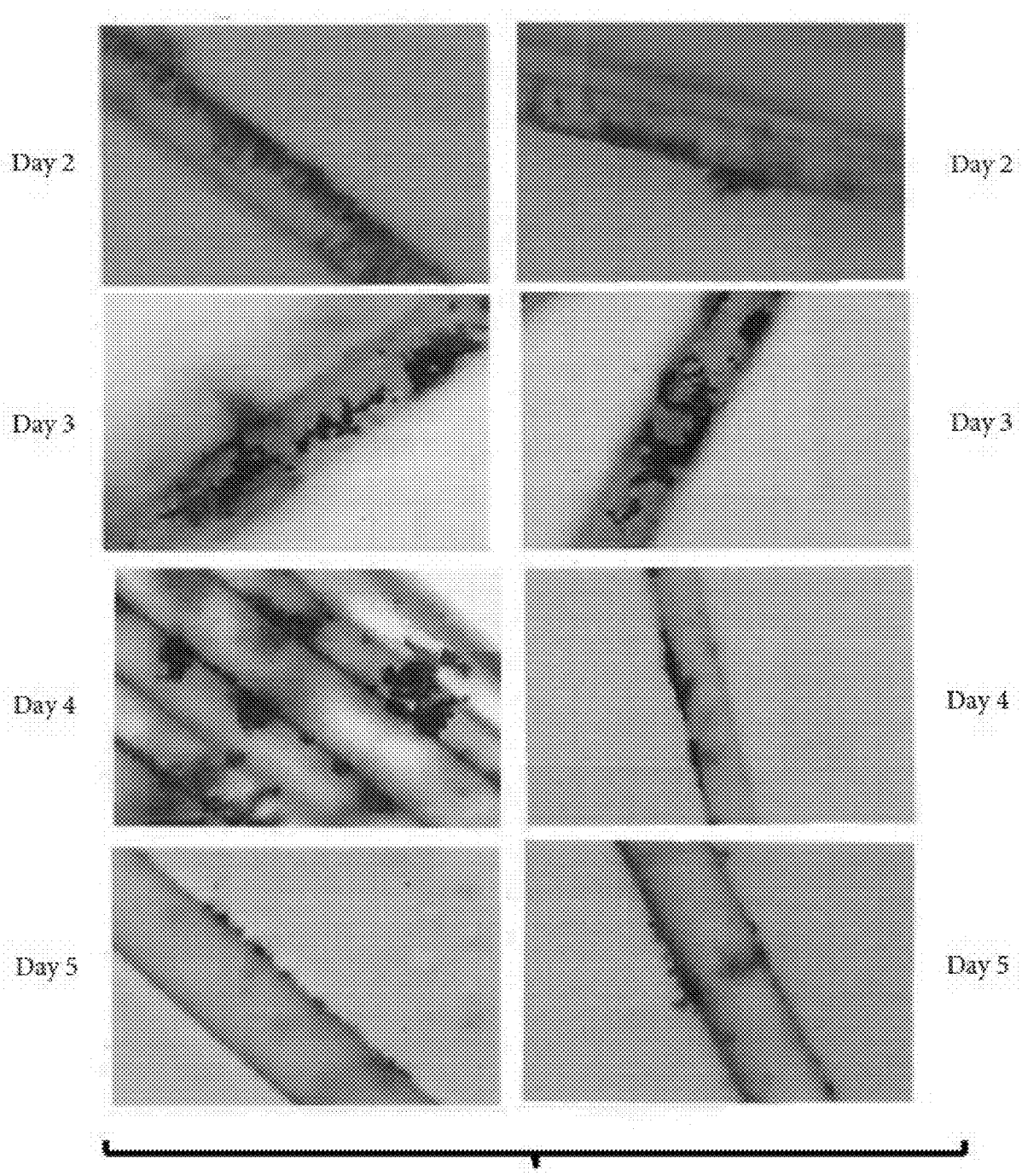
FIG. 3 illustrates biofilm growth of Lf Qi6 in substrates in scale-up culture.

SEQ ID NO: 1 is the amino acid sequence of the protein designated as "Qi611S."

SEQ ID NO: 2 is Qi611s, a nucleotide sequence encoding the amino acid sequence of SEQ ID NO: 1.

SEQ ID NO: 3 is a forward primer, "Lacto F," useful according to the subject invention.

SEQ ID NO: 4 is a reverse primer, "Lacto R," useful according to the subject invention.

SEQ ID NO: 5 is the nucleotide sequence for the cloning/expression region of the pET-15b vector.

SEQ ID NO: 6 is an amino acid sequence for a His-tagged recombinant protein encoded by the cloning/expression region of the pET-15b vector.

DETAILED DESCRIPTION OF THE INVENTION

The subject invention provides compositions and methods for inhibiting a viral infection and/or the symptoms thereof. Preferred embodiments of the invention provide pharmaceutical compositions, and methods of using the same, comprising a strain of *Lactobacillus fermentum* bacterium, and/or one or more bioactive extracts thereof. The subject invention also provides compositions comprising *L. fermentum* bacterium, and/or bioactive extracts thereof, in a lyophilized, freeze dried, and/or lysate form.

Advantageously, preferred compositions and treatment methods provided herein are effective in inhibiting viral infections, including by, in some embodiments, inducing protective innate immunity. In certain embodiments, the compositions of the subject invention can be used effectively in the treatment of acute and chronic viral infections. In a specific embodiment, the subject is infected, or at risk for infection, with a coronavirus. Such coronaviruses include, for example, Severe Acute Respiratory Syndrome associated Coronavirus (SARS-CoV), Middle East Respiratory Syndrome associated Coronavirus (MERS-CoV), and the SARS-CoV-2 virus discovered in late 2019.

In one aspect, the subject invention provides a pharmaceutical composition for inhibiting a viral infection, comprising an isolated bacterial strain, and/or a bioactive extract thereof, and, optionally, one or more pharmaceutically acceptable excipients. In some embodiments, the isolated and/or biologically pure strain is *Lactobacillus fermentum* Qi6, hereafter also referred to as Lf Qi6. In preferred embodiments, the pharmaceutical compositions provided herein comprise one or more bioactive extracts of Lf Qi6 obtained after it has been grown in the biofilm phenotype. Methods for growing biofilm are known in the art and are described in, for example, WO 2012/118535, which is incorporated herein, in its entirety, by reference, including the publications cited in that reference, such as those cited at pages 26-31.

The pharmaceutical compositions provided herein may also include other pharmaceutically-acceptable ingredients known to those skilled in the art, including, but not limited to, pharmaceutically-acceptable carriers, adjuvants, excipients, diluents, fillers, buffers, preservatives, anti-oxidants, lubricants, stabilisers, solubilisers, surfactants (e.g., wetting agents), masking agents, and colouring agents. The formulations may further comprise other active agents including, for example, other therapeutic or prophylactic agents.

In another aspect, the subject invention provides a method of inhibiting, via immunomodulation or otherwise, viral infections. The method preferably comprises administering, to a subject, a therapeutically effective amount of the pharmaceutical composition, the composition preferably comprising one or more bioactive extracts of a Lf Qi6 biofilm.

In preferred embodiments, the compositions of the subject invention exert their virus inhibiting activity via the innate immune system. Specifically, by acting upon signaling pathways, including, for example, cytokines and receptors, involved in inflammatory and/or other immune responses, the compositions of the subject invention can inhibit the ability of the virus to enter a cell and/or spread from one cell to another. In one embodiment, the immunomodulated proceeds via the involvement of PPAR agonism. In a preferred embodiment, the innate system can thus be primed to more effectively resist future infections by the same, or related, virus. The viral inhibitory activity may also be achieved via binding of a component of the composition to the ACE2 receptor, thereby blocking entry of the virus into a cell.

Selected Definitions

As used herein, reference to an "isolated" microbe refers to one that has been removed from materials with which it exists in nature. The microbe may be isolated from, for example, soil, blood, mucous, or milk such that it is removed from, and is no longer mixed or otherwise associated with, those materials to the extent that it is in nature. Such isolation can be used to impart upon the microbe markedly different characteristics, such as the production of different, or different amounts of, compounds, compared to what the microbe exhibits in its natural state.

As used here in, a "biologically pure culture" is one that has been isolated from other biologically active materials, including any materials with which it may have been associated in nature. In a preferred embodiment, the culture has been isolated from all other living cells. In further preferred embodiments, the biologically pure culture has advantageous characteristics compared to a culture of the same microbial species that may exist in nature. The advantageous characteristics can be, for example, enhanced production of one or more desirable growth by-products.

In certain embodiments, purified compounds are at least 60% by weight the compound of interest. Preferably, the preparation is at least 75%, more preferably at least 90%, and most preferably at least 99%, by weight the compound of interest. For example, a purified compound is preferably one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

As used herein the term "extract" refers to a composition obtained by processing a culture. The processing may involve, for example, physical and/or chemical treatment. The physical and/or chemical treatment may comprise, for example, filtering, centrifugation, sonication, pressure treatment, radiation treatment, lysing, treatment with solvents or other chemicals, and combinations of these treatments. The extract can be in the form of, for example, a supernatant such as that produced via centrifugation. The extract can also include cell mass obtained through centrifugation. The cells may be intact or not intact, viable or not viable. The extract may comprise cell membrane components and/or intracellular components. In certain embodiments, the extract is at least 80, 85, 90, or 95%, by weight, cell mass. In certain embodiments, at least 95% of the intact cells are non-viable. In certain embodiments, less than 10% of the cell mass in the extract is intact cells.

"Qi611S" refers to a protein having the amino acid sequence of SEQ ID NO: 1. Reference to a "Qi611S Protein," in the singular or plural, refers to Qi611S, as well as biologically-active fragments and variants of 611S.

As used herein, "gene" refers to a segment of DNA, or a nucleotide sequence, capable of expressing a polypeptide and/or amino acid chain. In certain embodiments, the gene includes regions, such as promoter regions, preceding and/or following a coding region.

As used herein, an "isolated" or "purified" compound is substantially free of other compounds, such as cellular material, with which it is associated in nature. A purified or isolated polynucleotide (ribonucleic acid (RNA) or deoxyribonucleic acid (DNA)) is free of sequences that flank it in its naturally-occurring state. A purified or isolated polypeptide is free of, for example, other cellular material with which it would be associated in nature. "Isolated" in the context of a microbial strain means that the strain is removed from the environment in which it exists in nature. Thus, the isolated strain may exist as, for example, a biologically pure culture, or as spores (or other forms of the strain) in association with a carrier.

As provided herein, "pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable excipient, carrier or adjuvant" refers to an excipient, carrier or adjuvant that can be administered to a subject, together with an active ingredient, and which does not destroy the pharmacological activity thereof and is nontoxic when administered in doses sufficient to deliver a therapeutic amount of the compositions provided herein. Except insofar as any conventional media or agent is incompatible with the active ingredient, its use in the therapeutic compositions of the invention is contemplated. Supplementary active ingredients can also be incorporated into the compositions.

Examples of carriers suitable for use in the pharmaceutical compositions are known in the art and such embodiments are within the purview of the invention. The pharmaceutically acceptable carriers and excipients, include, but are not limited to, aqueous vehicles, water-miscible vehicles, non-aqueous vehicles, stabilizers, solubility enhancers, isotonic agents, buffering agents, suspending and dispersing agents, wetting or emulsifying agents, complexing agents, sequestering or chelating agents, cryoprotectants, lyoprotectants, thickening agents, pH adjusting agents, and inert gases. Other suitable excipients or carriers include, but are not limited to, dextran, glucose, maltose, sorbitol, xylitol, fructose, sucrose, and trehalose.

"Planktonic" refers to a phenotype typical to microorganisms (bacteria, fungi, and/or protozoa, with associated bacteriophages and other viruses) that float freely in a liquid medium.

In some embodiments, Lf Qi6 can be grown in a biofilm phenotype. As used herein, a "biofilm" is a complex aggregate of microorganisms, such as bacteria, wherein the cells adhere to each other using a matrix usually composed of, but not limited to, polysaccharide material. The cells in biofilms have physiologically distinct properties compared to planktonic cells of the same organism, which are single cells that can float or swim in liquid or gaseous mediums, or reside on or in solid or semi-solid surfaces.

For the purpose of the present invention the abbreviation cfu shall designate a "colony forming unit" that is defined as the number of bacterial cells as revealed by microbiological counts on agar plates.

The term "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the infection, the symptom of the infection, or the risk of (or susceptibility to) the infection. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being.

The term "prevention" or any grammatical variation thereof (e.g., prevent, preventing, etc.), as used herein, includes but is not limited to, at least the reduction of likelihood of the risk of (or susceptibility to) acquiring an infection (e.g., causing at least one of the clinical symptoms of the disease not to develop in a patient that may be exposed to or predisposed to the disease but does not yet experience or display symptoms of the disease). The term "prevention" may refer to avoiding, delaying, forestalling, or minimizing one or more unwanted features associated with an infection, and/or completely or almost completely preventing the development of an infection and/or its symptoms altogether. Prevention can further include, but does not require, absolute or complete prevention, meaning a condition may still develop at a later time and/or with a lesser severity than it would without preventative measures. Prevention can include reducing the severity of the onset of a disease or disorder, and/or inhibiting the progression thereof.

"Inhibition" includes direct antiviral activity against the virus, as well as directly or indirectly reducing the ability of a virus to enter a cell and/or reducing the ability of a virus to spread from one cell to another. The indirect activity may be achieved via, for example, immunomodulation.

"Immunomodulation," as contemplated by the current invention, preferably involves stimulation of innate immunity. This can involve, for example, modulation of cytokine production and/or activity as well as, in certain embodiments modulation of cellular metabolism to disfavor viral entry or replication. The modulation of cellular metabolism may be achieved by, for example, shifting mitochondrial metabolism away from sugar based metabolism to, for example, lipid based metabolism.

As used herein, the term "subject" refers to an animal. The animal may be, for example, a human, pig, horse, goat, cat, mouse, rat, dog, ape, fish, chimpanzee, orangutan, guinea pig, hamster, cow, sheep, bird (including chicken), as well as any other vertebrate or invertebrate.

The preferred subject, in the context of this invention, is a human of any age and/or gender. In some embodiments, the subject is suffering from a health condition, disease, or disorder, while, in some embodiments, the subject is in a state of good health (e.g., free from injury or illness) but desires enhanced health and/or functioning of a particular organ, tissue, or body system.

Administration of the pharmaceutical compositions provided herein is preferably in a "therapeutically effective amount," this being an amount sufficient to result in a biological or medical response of a cell, tissue, system, animal, or human that is being treated. The actual amount administered, and the rate and time-course of administration, will depend on the nature and severity of the infection being treated as well as the subject. Prescription of treatment, e.g., decisions on dosage etc, is within the responsibility of general practitioners and other medical doctors, and typically takes into account the disorder to be treated, the condition of the individual patient, the site of delivery, the method of administration and other factors known to practitioners.

Ranges provided herein are understood to be shorthand for all of the values within the range. For example, a range of 1 to 20 is understood to include any number, combination of numbers, or sub-range from the group consisting of 1, 2, 3, 4, 5, 6, 7, 8, 9, 10, 11, 12, 13, 14, 15, 16, 17, 18, 19, 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, "recombinant" cells are modified by the introduction of a heterologous nucleic acid, or the alteration of a native nucleic acid. Thus, for example, recombinant cells can express genes that are not found within the native (non-recombinant) form of the cell or express native genes that are otherwise abnormally expressed, under-expressed or not expressed at all.

As used herein, "reduce" refers to a negative alteration, and the term "increase" refers to a positive alteration, each of at least 1%, 5%, 10%, 25%, 50%, 75%, or 100%.

As used herein, "reference" refers to a standard or control condition.

The transitional term "comprising," which is synonymous with "including," or "containing," is inclusive or open-ended and does not exclude additional elements or method steps not recited. By contrast, the transitional phrase "consisting of" excludes any element, step, or ingredient not specified in the claim. The transitional phrase, "consisting essentially of," limits the scope of a claim to the specified materials or steps "and those that do not materially affect the basic and novel characteristic(s)" of the claimed invention, e.g., the ability to preclude bacterial growth. Use of the term "comprising" contemplates embodiments "consisting" and "consisting essentially" of the recited component(s).

Unless specifically stated or is obvious from context, as used herein, the term "or" is understood to be inclusive. Unless specifically stated or is obvious from context, as used herein, the terms "a," "an," and "the" are understood to be singular or plural.

Unless specifically stated or is obvious from context, as used herein, the term "about" is understood as within a range of normal tolerance in the art, for example, within 2 standard deviations of the mean. The term "about" can be understood as within 10%, 9%, 8%, 7%, 6%, 5%, 4%, 3%, 2%, 1%, 0.5%, 0.1%, 0.05%, or 0.01% of the stated value.

Lactobacillus spp. and the Qi601S Lysate

Lactobacillus spp. are Gram-positive rods that are often found in fermented foods such as cheeses. Many strains are identified as probiotic because the bacteria are nonpathogenic and can inhibit pathogenic bacteria proliferation in a subject, and reduction of cholesterol.

In some embodiments, the bacterial strain is Lactobacillus fermentum Qi6, also referred to herein as LfQi6. Lactobacillus fermentum is a Gram-positive rod. Lactobacillus fermentum Qi6 (Lf Qi6) can be grown in MRS media at 37° C. In one embodiment, the subject invention provides an isolated or a biologically pure culture of LfQi6. In another embodiment, the subject invention provides a biologically pure culture of LfQi6, grown as a biofilm. Specifically taught herein are methods for inducing and identifying the biofilm phenotype. Further provided herein are methods of utilizing the biofilm phenotype, as well as extracts of the biofilm phenotype, including lysates thereof. In preferred embodiments, the pharmaceutical compositions comprise bioactive extracts of LfQi6 biofilm.

A culture of the L. fermentum microbe has been deposited with the American Type Culture Collection (ATCC), 10801 University Blvd., Manassas, Va. 20110-2209 USA. The deposit has been assigned accession number ATCC No. PTA-122195 by the repository and was deposited on Jun. 10, 2015.

The subject culture has been deposited under conditions that assure that access to the culture will be available during the pendency of this patent application to one determined by the Commissioner of Patents and Trademarks to be entitled thereto under 37 CFR 1.14 and 35 U.S.C 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

*Lactobacillus fermentum* Qi6 (Lf Qi6) can be grown in MRS media at 37° C. Lf Qi6 is a proprietary strain. The Lf Qi6 culture can be used in the presently presented disclosure or bioactive lysates can be isolated from the Lf Qi6 culture directly and used in antiviral methods and compositions.

Additionally, Lf Qi6 can be grown in a biofilm phenotype. The Lf Qi6 culture can be used in the presently presented disclosure or bioactive lysates can be isolated from the Lf Qi6 biofilm culture and used in the antibacterial or other barrier enhancing/creating methods and compositions.

One method to grow the culture to form a biofilm, the culture can be incubated in 5 ml of MRS broth for 24 hour at 37° C. 1 ml of the culture can then be transferred into a T-150 tissue culture plate with 25 ml of MRS broth. 25 ml of MRS media can then be changed every 48 hours to allow the biofilm of Lf Qi6 to grow as lawn on the bottom of the culture plate. The culture can then be grown for 7 days to produce a thick biofilm layer. The grown biofilm layer can be subsequently scraped out and suspended in fresh medium. Freezer stacks can be made with glycerol and stored in –80° C.

A biofilm phenotype of Lf Qi6 in frozen stock can be cultured in 10 ml of fresh MRS media for 24 hour at 37° C. 10 ml of culture can be inoculated into 25 L of MRS media with 500 g of sterile glass wool. The biofilm can then be cultured for 72 hours under static conditions at 37° C. The culture can be mixed every 24 hours with a gentle shaking, after which the media and glass wool can be harvested. The biofilm cells can be subsequently detached from the glass wool via sonication. The cells can be further centrifuged to concentrate the biofilm of Lf Qi6, which was then suspended in sterile water. This scale-up yields a biofilm culture at a concentration of 2 g/L.

Qi611S Proteins and Polynucleotide Sequences Encoding 611S Proteins

In preferred embodiments, the present invention provides a protein, as well as fragments and variants thereof, useful for inhibiting a viral infection. The present invention further provides nucleotide sequences that encode the protein, as well as fragments and variants thereof.

In certain specific embodiments, a protein of the present invention, referred to as "Qi611S," has a molecular weight of about 8.0 kDA. "Qi611S proteins", which include Qi611S and biologically-active fragments and variants thereof, can be characterized according to several parameters, including biological activities, such as, for example: antiviral activity and enhancing innate immune functions.

In certain embodiments, Qi611S Proteins can, directly or indirectly, induce expression of, and/or act as an agonist toward, one or more molecules selected from, for example, peroxisome proliferator-activated receptors (PPARs) (e.g., PPARα, PPARβ/δ, and/or PPARγ); extracellular signal-regulated kinases (ERK 1/2); and glucocorticoid receptors (GR).

Modulation of PPARs, ERK and GR can have downstream immunomodulatory effects. Thus, in certain embodiments, the composition of the subject invention can be used for inhibiting viral infections by modulating one or more biological pathways involving PPAR, ERK and/or GR.

A Qi611S Protein can further be defined by its amino acid sequence. In a specific embodiment (Qi611S), the protein has the 74 amino acid sequence shown as SEQ ID NO: 1.

In certain embodiments, the proteins provided herein can also be identified based on immunoreactivity with certain antibodies, as well as other methods described below.

In certain embodiments, Qi611S Proteins are produced by the *Lactobacillus fermentum* Qi6 bacterial strain when laboratory growth conditions are used to force the growth into a biofilm phenotype. In preferred embodiment, this bacterial strain possesses the Qi611S DNA sequence (SEQ ID NO: 2), which is capable, under biofilm phenotype conditions, of expressing a protein having SEQ ID NO: 1.

In further embodiments, a polynucleotide encoding a Qi611S Protein can be defined by, for example, the ability to hybridize with, or be amplified by, certain exemplified probes and primers (e.g., SEQ ID NOs: 3-4).

In certain embodiments, the present invention provides isolated polynucleotide sequences, or genes, that encode the Qi611S Proteins. Furthermore, in some embodiments, the present invention provides methods for using the polynucleotide sequences to produce recombinant hosts that express a Qi611S Protein.

In certain embodiments, the polynucleotide sequence is Qi611S, which is 222 base pairs and encodes Qi611S; however, in certain embodiments, different DNA sequences can encode the amino acid sequences disclosed herein because of, for example, the redundancy of the genetic code. It is well within the skill of a skilled artisan to create these alternative DNA sequences encoding the Qi611S Proteins.

As used herein, "variants" of a protein refer to sequences that have one or more amino acid substitutions, deletions, additions, or insertions. In preferred embodiments, these substitutions, deletions, additions or insertions do not materially adversely affect the therapeutic and/or cosmetic activity of Qi611S. Variants that retain one or more biological activities of Qi611S are within the scope of the present invention. Preferably the one or more biological activities are selected from antiviral activity and enhancing innate immune functions.

"Fragments" of Qi611S and its variants are also within the scope of Qi611S Proteins, so long as the fragment retains one or more biological properties of Qi611S. Preferably the one or more biological activities are selected from antiviral activity and enhancing innate immune functions. Preferably, the fragment is at least 10%, 15%, 20%, 25%, 30%, 35%, 40%, 45%, 50%, 55%, 60%, 65%, 70%, 75%, 80%, 85%, 90%, 95%, 96%, 97%, 98%, or 99% of the full length Qi611S. The fragment may comprise, for example, one or more hydrophilic domains of Qi611S or variant. These domains may be directly connected with intervening amino acids removed. Hydrophilic domains can be readily identified using standard procedures known in the art.

The subject invention further contemplates fusion constructs where a Qi611S Protein is attached, directly or indirectly (e.g., via a linker), to another moiety that may be, for example, a targeting moiety (e.g., ligand, antibody, or aptamer), a carrier, a label, or an activity enhancer.

The subject invention further contemplates antibodies (e.g., polyclonal, monoclonal, chimeric, and humanized) to the Qi611S Proteins. These antibodies can be readily prepared by a person of ordinary skill in the art having possession of the teachings provided herein. These antibodies can be used for, for example, therapies, diagnostics, and protein purification.

In certain embodiments, a polynucleotide encoding a Qi611S Protein can be isolated, amplified and ligated into a vector. A "vector," "plasmid," or "plasmid vector" is a DNA molecule used to transfer DNA to a cell, often from one cell to another (a host cell). The vector can be replicated in the host cell; or, the vector can be a means to incorporate DNA into (or remove DNA from) a cell. A variety of means can be used to introduce a vector into a host cell. Some cells can uptake a vector without any action by one skilled in the art other than placing the vector in the cell culture. Others require chemical modification. Regardless of the means with which a cell can uptake a vector, once a host cell has the ability to do so, it is now a "competent" cell.

Figure 9:
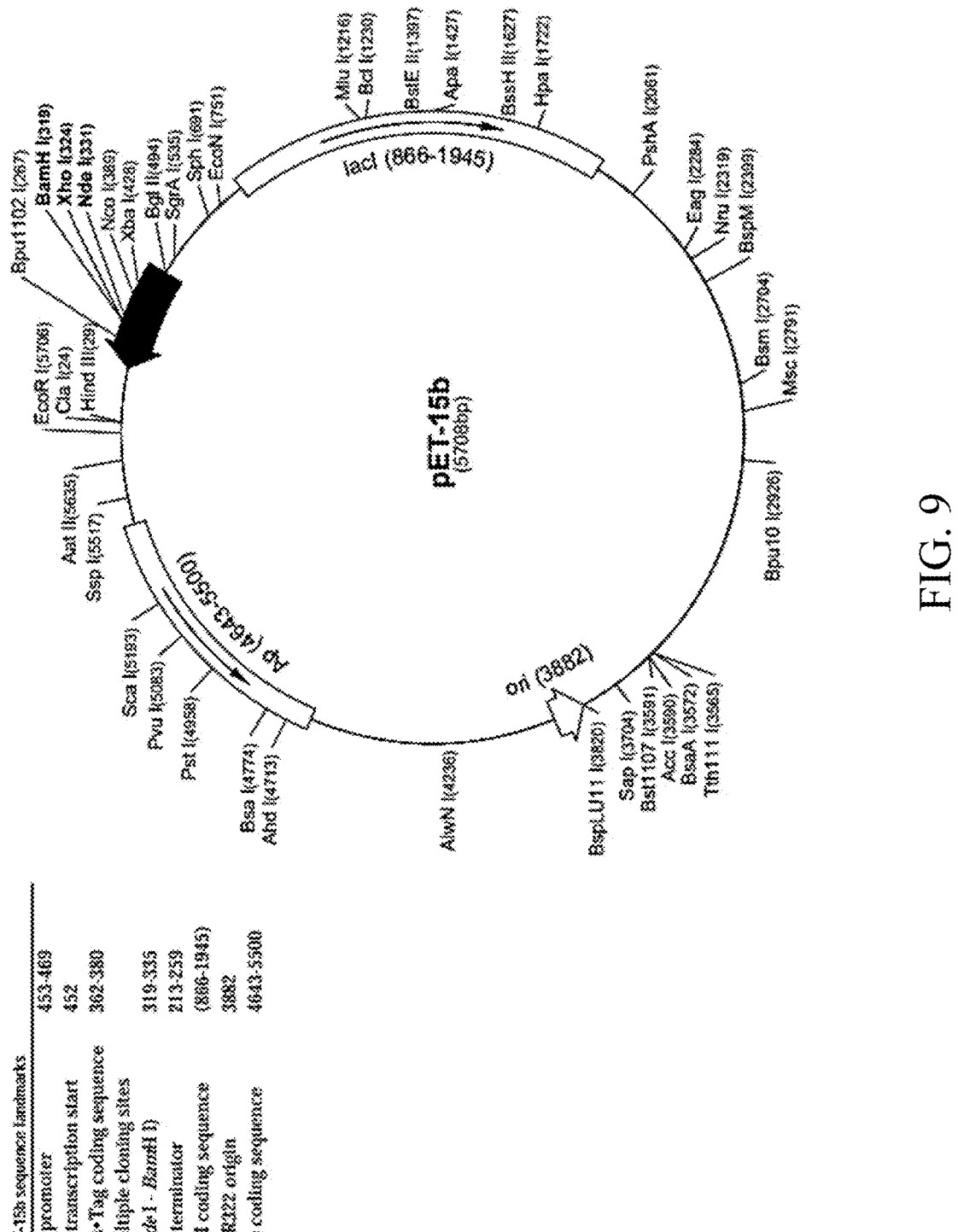
FIG. 9 shows a map of the pET-15b vector utilized according to embodiments of the present invention.
Figure 10:
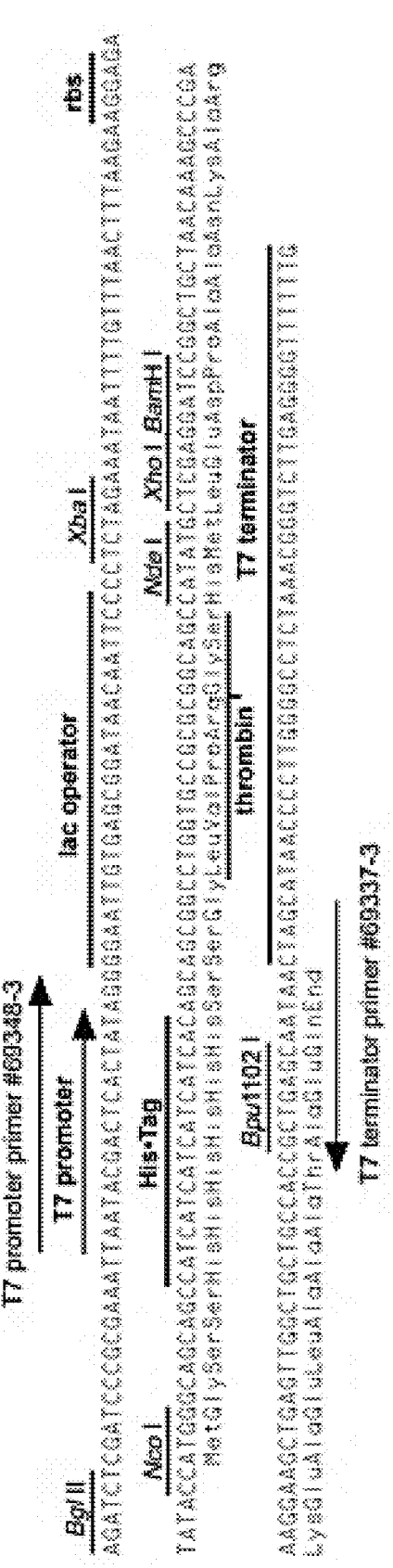
FIG. 10 shows the pET-15b cloning/expression region of the coding strand transcribed by T7 RNA polymerase.
Figure 15:
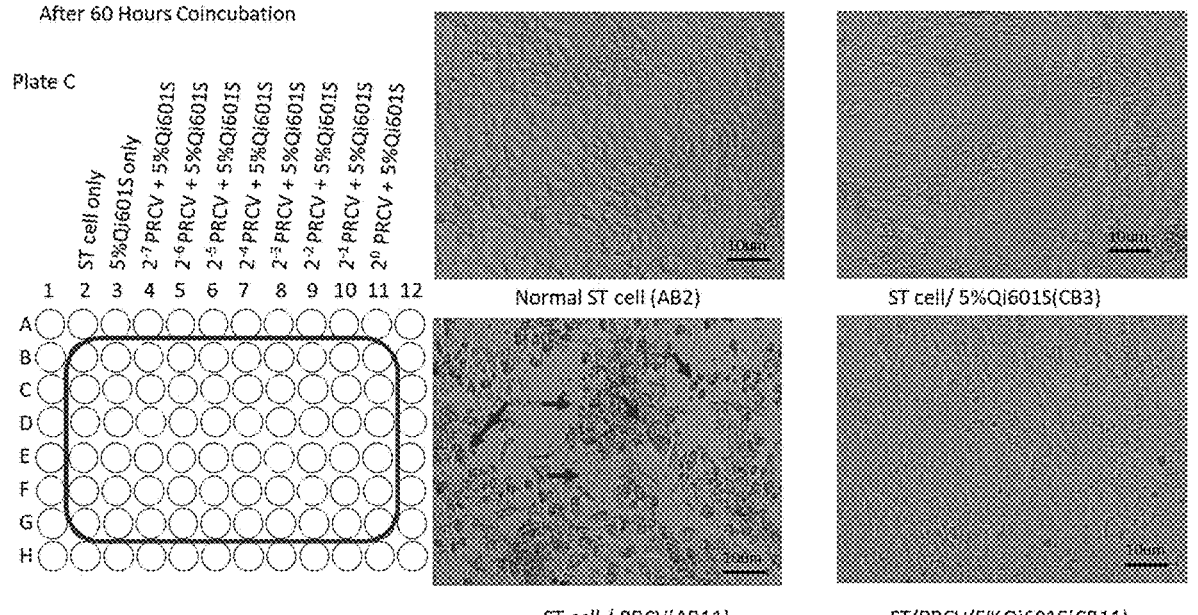

One example of a commercially available vector is pET-15b, in which, using restriction enzyme digestion, one skilled in the art can create a vector carrying Qi611S, or other polynucleotide encoding a Qi611S Protein. The pET-15b vector carries an N-terminal HisTag® sequence followed by a thrombin site and three cloning sites (SEQ ID NO. 6). Unique sites are shown on the circle map depicted in FIG. 9. The cloning/expression region of the coding strand transcribed by T7 RNA polymerase is shown in FIG. 10 (SEQ ID NO. 5).

In certain embodiments, the present invention pertains to the genetic transformation of host cells so as to provide these cells with the ability to produce a Qi611S protein. For example, a vector with Qi611S (or other polynucleotide encoding a Qi611S Protein) can be transformed into a host cell (e.g., a microorganism, a plant, a fungal, and/or an animal cell) allowing for the use of recombinant cells for the production of the Qi611S Protein.

In preferred embodiments, the host cell is a strain of *Escherichia coli*, e.g., *E. coli* BL21 or *E. coli* C43. Alternatively, the ability to transform cells, other than *E. coli*, into competent cells is well understood in the art, this includes cells chosen based on, e.g., their transformation ability, ability and efficiency for heterologous protein expression, stability of the protein in the host, presence of auxiliary genetic capabilities, lack of mammalian toxicity, ease of killing and fixing without damage to the protein, ease of cultivation and/or formulation, ease of handling, economics, storage stability and the like.

The present invention also provides methods of producing a Qi611S Protein by cultivating a host cell transformed with a polynucleotide of the present invention (e.g., SEQ ID NO: 2) under conditions that allow for the expression of the polypeptide and, optionally, recovering the expressed polypeptide.

In certain embodiments, the host cell is transformed to express the polypeptide in enhanced amounts. For example, the DNA vector can include a strong transcriptional promoter sequence closely preceding the gene to be cloned. In certain embodiments, the strong promoter is a trp operon, a lac operon, a T7 promoter, and/or a pL promoter.

It will be recognized by those skilled in the art that DNA sequences of the subject invention may vary due to the degeneracy of the genetic code and codon usage. All DNA sequences that encode a Qi611S Protein are contemplated. Thus, all polynucleotide sequences that encode a Qi611S Protein are included in this invention, including DNA (optionally including an ATG preceding the coding region) that encodes SEQ ID NO: 1. The subject invention also includes polynucleotides having codons that are optimized for expression in a host cell, including any of the specific types of cells referred to herein. Various techniques for creating optimized sequences are known in the art.

Additionally, it will be recognized by those skilled in the art that allelic variations may occur in the DNA sequences that will not significantly change activity of the amino acid sequences of the peptides that the DNA sequences encode. All such variant DNA sequences are included within the scope of this invention.

The skilled artisan will understand that the exemplified sequences can be used to identify, produce, and use additional nucleotide sequences that encode Qi611S Proteins. Variant DNA sequences having at least 90%, or at least 95% identity to a recited DNA sequence and encoding a Qi611S Protein are included in the subject invention. Other numeric ranges for variant polynucleotides and amino acid sequences are provided below (e.g., 50-99%). Following the teachings herein and using knowledge and techniques well known in the art, the skilled worker will be able to make a large number of operative embodiments having variant DNA sequences without the use of undue experimentation. Specifically contemplated are homologs from other strains or species.

The fragments and the mutational, insertional, and deletional variants of the polynucleotide and amino acid sequences of the invention can be used in the same manner as the exemplified sequences so long as the fragments and variants have substantial sequence similarity with the original sequence. As used herein, substantial sequence similarity refers to the extent of nucleotide or amino acid sequence similarity that is sufficient to enable the variant or fragment sequence to function in the capacity as the original sequence. Preferably, this similarity is greater than 50%; more preferably, this similarity is greater than 75%; and most preferably, this similarity is greater than 90%. The degree of similarity needed for the variant to function in its intended capacity will depend upon the intended use of the sequence. It is well within the skill of a person trained in this art to make mutational, insertional, and deletional mutations that are designed to improve the function of the sequence or otherwise provide a methodological advantage. The identity and/or similarity can also be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein.

The amino acid identity/similarity and/or homology will typically be highest in critical regions of the protein that account for biological activity and/or are involved in the determination of three-dimensional configuration that ultimately is responsible for the biological activity. In this regard, certain amino acid substitutions are acceptable and can be expected if these substitutions are in regions that are not critical to activity or are conservative amino acid substitutions that do not affect the three-dimensional configuration of the molecule. For example, amino acids may be placed in the following classes: non-polar, uncharged polar, basic, and acidic. Conservative substitutions, whereby an amino acid of one class is replaced with another amino acid of the same type, fall within the scope of the subject invention so long as the substitution does not materially alter the biological activity of the compound. The following (Table 1) is a list of examples of amino acids belonging to each class.

TABLE 1

Classification of amino acids based on physical properties.

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the protein.

Viruses and Diseases Treated

In one embodiment, the compositions and methods of the subject invention can be used to inhibit a viral infection caused by, for example, an RNA virus including retroviruses (e.g., lentiviruses such as HIV) and coronavirus (e.g., the virus that causes COVID-19). Examples of RNA viruses include, but are not limited to, Orthomyxoviruses, Adenovirus, Hepatitis C Virus (HCV), Zika, the virus that causes COVID-19, Dengue, Ebola, Influenza A/B/C virus, polio measles, primate foamy virus, HIV, SARS-CoV (Severe Acute Respiratory Syndrome-Corona Virus), CoV MERS (Middle East Respiratory Syndrome virus), HCoV-NL63, HCoV-0C43, HCoV-229E, HCoV-HKU1, adult T-cell leukemia virus (ATLV), Human T-cell lymphotropic virus type 1 (HTLV-1), and type II (HTLV-2). Furthermore, inhibition of mutated and/or truncated viruses derived from the above viruses are encompassed by the present invention.

SARS-CoV, MERS-CoV and SARS-CoV-2 are all highly pathogenic human coronaviruses responsible for acute and chronic diseases of, for example, the respiratory, hepatic, gastrointestinal and neurological systems. It is envisaged that the administration of a composition of the subject invention may be used for the treatment and/or prevention of any infection caused by any coronavirus.

In a particular embodiment, the coronavirus may be SARS-CoV. In another embodiment, the coronavirus may be MERS-CoV. In a preferred embodiment, the coronavirus may be SARS-CoV-2.

Other viruses include, for example, avian leukemia virus, avian sarcoma virus, avian reticuloendotheliosis virus, murine mammary cancer virus, murine leukemia virus, murine sarcoma virus, guinea pig type C virus, hamster type C virus, rat leukemia virus, feline leukemia virus, feline sarcoma virus, feline type C virus, ovine leukemia virus, bovine leukemia virus, swine type C virus, simian leukemia virus, Mason-Pfizer virus, simian sarcoma virus, simian T-lymphotropic virus, baboon type C virus, visna virus, EIAV, spuma virus, ovine progressive pneumonia virus, ovine maedi virus, simian T-lymphotropic virus type III (STLV-III), equine infectious anemia virus, Bovine immunodeficiency virus (BIV), the Feline immunodeficiency virus (Hy), the Simian immunodeficiency virus (SIV), feline Coronavirus (FCoV), and Mouse Hepatitis Virus (MHV-LUC).

In one embodiment, the subject invention provides methods for preventing and/or treating a disease, or symptoms of a disease, caused by a virus, e.g., a retrovirus or coronavirus. The method comprises administering the composition of the subject invention to a subject in need of such prevention and/or treatment.

In one embodiment, the disease may be, for example, Zika, Ebola, Hepatitis C, Influenza, COVID-19, MERS, SARS, AIDS, adult T-cell lymphoma (ATL), Dengue fever, and progressive general lymphadenosis (PGL). Preferably, the disease is COVID-19.

Pharmaceutical Compositions of the Subject Invention

A composition of the subject invention may be administered alone or in combination with other treatments, either simultaneously or sequentially dependent upon the condition to be treated. The pharmaceutical compositions provided herein may be dissolved in, suspended in, or admixed with one or more other pharmaceutically acceptable ingredients. The compositions may also be presented in a liposome or other microparticle.

The pharmaceutical compositions provided herein may contain a single (unit) dose of bacteria, or lysate, or extract thereof. Suitable doses of bacteria (intact, lysed or extracted) may be in the range 104 to 1012 cfu, e.g., one of 104 to 1010, 104 to 108, 106 to 1012, 106 to 1010, or 106 to 108 cfu. In some embodiments, doses may be administered once or twice daily. In some embodiments, a composition for use according to the present invention may comprise at least about 0.01%, about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0% by weight of the Lf Qi6 extracts. In some embodiments, the compositions may comprise, one of at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to 10 about 5%, by weight of the Lf Qi6 extracts.

The compositions are preferably formulated into suitable pharmaceutical preparations such as aerosols, inhalants, tablets, capsules, or elixirs for oral administration or in sterile solutions or suspensions for parenteral administration.

In one embodiment, the composition according to the invention, together with a conventional adjuvant, carrier, or diluent, may thus be placed into the form of solids including pills, troches, tablets, cachets, lozenges, filled capsules, powder and pellet forms, and liquids such as aqueous or non-aqueous solutions, suspensions, emulsions, elixirs, and capsules filled with the same. The composition may further comprise conventional ingredients in conventional proportions, with or without additional active compounds.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added. Various other materials may be present as coatings or for otherwise modifying the physical form of the solid unit dosage form. For instance, tablets, pills, or capsules may be coated with gelatin, wax, shellac, or sugar, and the like.

The pharmaceutical dosage forms suitable for injection or infusion can include sterile aqueous solutions or dispersions or sterile powders comprising the biopolymer-based hydrogel nanoparticles and microparticles. Preferably, the ultimate dosage form should be sterile, fluid, and stable under the conditions of manufacture and storage. The liquid carrier or vehicle can be a solvent or liquid dispersion medium comprising, for example, water, a polyol (for example, glycerol, propylene glycol, liquid polyethylene glycols, and the like), vegetable oils, nontoxic glyceryl esters, and suitable mixtures thereof.

Pharmaceutical compositions for topical administration can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like.

Pharmaceutical compositions suitable for intra-nasal administration are also encompassed by the present invention. Such intra-nasal compositions comprise the active composition in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol. The active composition may be combined with an inert powdered carrier and inhaled by the subject or insufflated.

Pharmaceutical compositions for administration by inhalation or insufflation can be provided in the form of a dry powder composition, and a suitable powder base such as lactose or starch. Such powder composition can be provided in unit dosage form, for example, in capsules, cartridges, gelatin packs, or blister packs, from which the powder can be administered with the aid of an inhalator or insufflator. In a preferred embodiment, the compositions are administered in an inhalant form.

In one embodiment, the composition is formulated in accordance with routine procedures as a pharmaceutical composition adapted for local administration to humans. Typically, compositions for local administration are solutions in a sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

In some embodiments the composition may be administered in an intradermal injection via a microneedle device comprising a plurality of needles. In another embodiment, the plurality of microneedles may be deployed in a line, square, circle, grid, or array. In other embodiments, the microneedle device may include between 2 and 2000 microneedles per square centimetre, such as between 4 and 1500 microneedles per square centimetre, of between 10 and 1000 microneedles per square centimetre. In a further embodiment, the microneedles may be between 2 and 2000 microns in length, such as between 20 and 1000 microns, or between 50 and 500 microns, or between 100 and 400 microns.

In some embodiments, the microneedles are solid. In other embodiments, the microneedles are hollow. In a further embodiment, the microneedles may be configured to deliver the composition intradermally, optionally wherein said immunomodulator is delivered to the lymphatic vessels. In yet a further embodiment, the composition may be coated onto or embedded within at least a portion of the microneedles, optionally wherein the microneedles are implanted into or removable from the skin. Preferably, said coating or microneedle would be dissolvable upon contact with the skin.

Methods of Administration

In certain embodiments, the compositions of the subjection invention may be administered by inhalation, orally, intra-nasally, topically, intramuscularly, subcutaneously, intrathecally, intravenously or intraperitoneally by infusion or injection.

In some embodiments of the invention, the composition may be administered via a single-use pre-filled syringe. In other embodiments, the composition may be administered via an automated, multi-use, or disposable cartridge jet injector, such as the 'Tropis ID' (WHO approved for polio) and 'Stratis' device, which is FDA approved for flu (both ex Pharmajet).

In some embodiments of the present invention, the composition may be administered for the treatment or prevention of infections caused by a virus in combination with one or more other antiviral therapies. Such antiviral therapies may include administration of oseltamivir phosphate (Tamiflu®), zanamivir (Relenza®), peramivir (Rapivab®), baloxavir marboxil (Xofluza®), or lopinavir/ritonavir (Aluvia®). Such antiviral therapies may be administered simultaneously, separately or sequentially with the subject composition. In a further embodiment, the antiviral therapy is administered via the same or different route of administration as the subject composition.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day.

The compositions can be conveniently administered in unit dosage form, containing for example, about 0.05 to about 10000 mg, about 0.5 to about 10000 mg, about 5 to about 1000 mg, or about 50 to about 500 mg of the active ingredient per unit dosage form.

The compositions may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations.

The composition may be used in prophylaxis of populations in general, but also those at high risk of virus infection, including health care workers and persons who have been in close contact to infected patients, as well as the elderly. Such prophylaxis may be achieved by changing the immune surveillance status and disease trajectory. It is also envisaged that an immunomodulating composition of the present invention may be used as a co-treatment of already infected patients.

Optionally, the pharmaceutical compositions of the present invention can include one or more other therapeutic agents, e.g., as a combination therapy. The additional therapeutic agent(s) will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy.

All patents, patent applications, provisional applications, and publications referred to or cited herein are incorporated by reference in their entirety, including all figures and tables, to the extent they are not inconsistent with the explicit teachings of this specification.

Materials and Methods

Culture of Lf Qi6 Biofilm

FIG. 1 shows procedures for seeding the Lf Qi6 culture. After being isolated and identified, Lf Qi6 was cultured in MRS agar plate. The culture was then incubated in 5 ml of MRS broth for 24 hour at 37° C. 1 ml of the culture was transferred into a T-150 tissue culture plate with 25 ml of MRS broth. 25 ml of MRS media was changed every 48 hours to allow the biofilm of Lf Qi6 to grow as lawn on the bottom of the culture plate. The culture was then grown for 7 days to produce a thick biofilm layer. The grown biofilm layer was subsequently scraped out and suspended in fresh medium. Freezer stacks were made with glycerol and stored in −80°.

A scaled-up production of Lf Qi6 biofilm is illustrated in FIG. 2. A biofilm phenotype of Lf Qi6 in frozen stock was cultured in 10 ml of fresh MRS media for 24 hour at 37°. 10 ml of culture was inoculated into 25 L of MRS media with 500 g sterile glass wool. The biofilm w then cultured for 72 hours under static conditions at 37° C. The culture was mixed every 24 hours with a gentle shaking, after which the media and glass wool were harvested. The biofilm cells were subsequently detached from the glass wool via sonication. The cells were further centrifuged to concentrate the biofilm of Lf Qi6, which was then suspended in sterile water. This scale-up yields a biofilm culture at a concentration of 50 g/25 L. The Lf Qi6 biofilm growth is further illustrated in FIG. 3, wherein the biofilm was cultured on substrates in a scaled-up culture as described herein.

Lf Qi6 Biofilm Downstream Processing

The downstream processing of Lf Qi6 biofilm is shown in FIG. 4. 50 g of biofilm phenotype of Lf Qi6 was suspended in 1 L of sterile water. The suspension was gently mixed for 24 hours at room temperature to allow the passive release of multiple bioactives. The mixture was then sonicated for 30 minutes (50 KHz, 200 watt) into uniform lysate using an Omni Sonic Ruptor 400. The sonicated lysate was then frozen and lyophilized into a fine powder.

Preparation of Lf Qi6 from Probiotic Bacteria

*L. fermentum* Qi6 was grown in MRS media using proprietary culture methods. Bacteria were then subcultured into 500ml MRS medium for an additional period, again using proprietary culture methods. Bacteria were sonicated (Reliance Sonic 550, STEMS Corporation, Mentor, OH, USA), centrifuged at 10,000 g, cell pellets dispersed in sterile water, harvested cells lysed (Sonic Ruptor 400, OMNI International, Kennesaw, GA, USA) and centrifuged again at 10,000 g, and soluble fraction centrifuged (50 kDa Amicon Ultra membrane filter, EMD Millipore Corporation, Darmstadt, Germany, Cat #UFC905008). The resulting fraction was distributed into 0.5 ml aliquots, flash frozen in liquid nitrogen and stored at −80° C.

Following are examples that illustrate procedures for practicing the invention. These examples should not be construed as limiting.

Example 1—Lf Qi6 Biofilm Phenotype Differs from the Planktonic Phenotype

Figure 5:
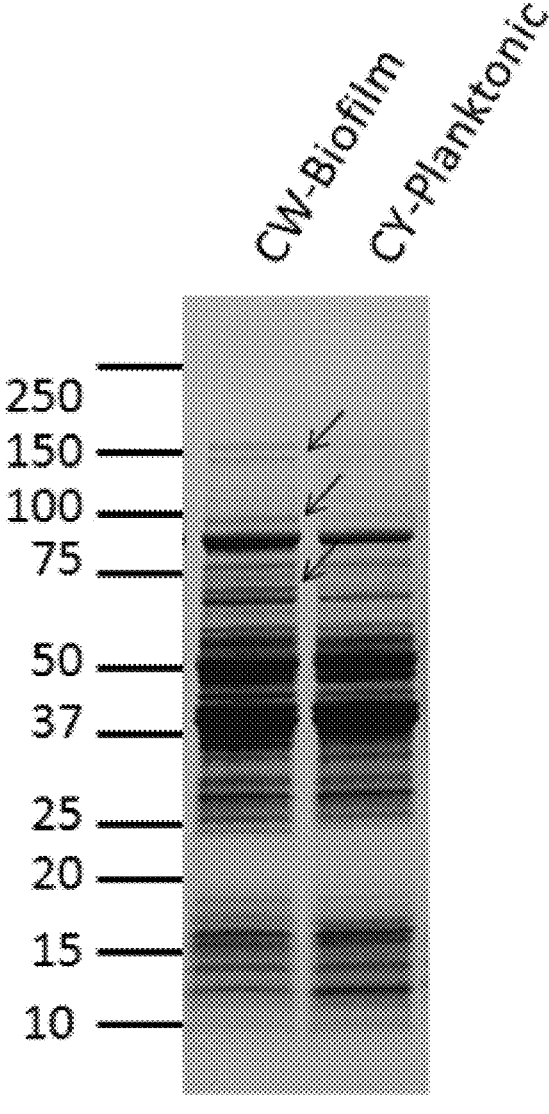
FIG. 5 illustrates SDS bands showing unique proteins in bioextract prepared from Lf Qi6 biofilm phenotype. Arrows show unique proteins in biofilm phenotype compared to planktonic phenotype.
Figure 6:
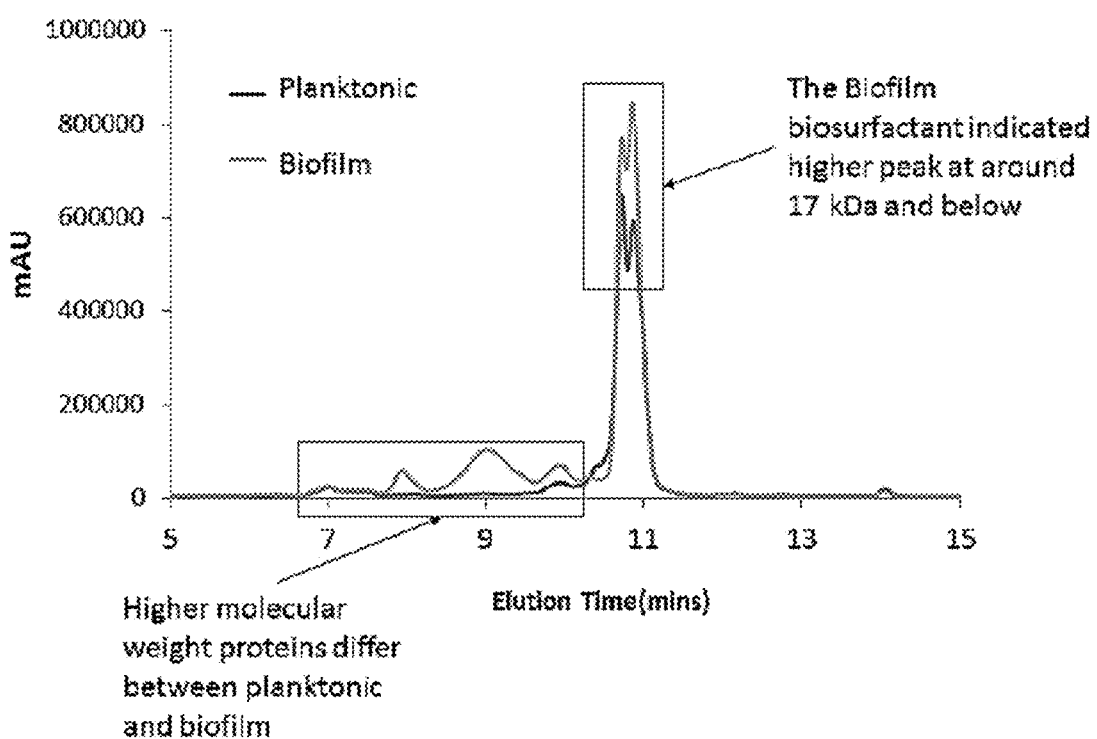
FIG. 6 illustrates size-exclusion HPLC showing unique proteins in bioextract prepared from Lf Qi6 biofilm phenotype.
Figure 7:
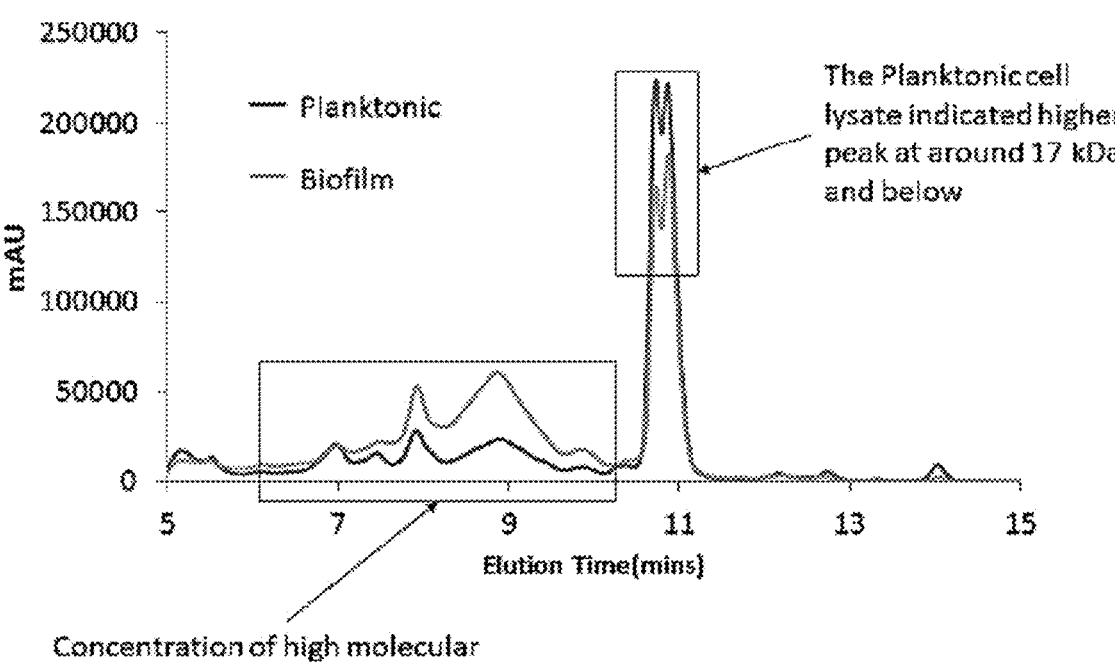
FIG. 7 illustrates size-exclusion HPLC showing unique proteins in bioextract prepared from Lf Qi6 biofilm phenotype.

Product extraction and protein estimation demonstrate different protein levels between the biofilm and planktonic phenotypes, as seen in Table 2 below. SDS data in FIG. 5 further corroborate such differences, as shown by extra bands expressed in the Lf Qi6 biofilm phenotype that are not present in the planktonic phenotype, indicative of unique proteins in the bioextract of the biofilm. Size-exclusion HPLC data in FIGS. 6 and 7 illustrate differences in molecular weight between proteins in bioextract prepared from Lf Qi6 biofilm and planktonic phenotype.

TABLE 2

Product extraction and protein estimation from biofilm and planktonic shows different protein levels.

| | Sample No. | Description | Extract Yield (g/L) | Protein Yield (g/L) | Protein % In Extract |
|---|---|---|---|---|---|
| Pellet | 1 | Planktonic | 0.4 | 0.2 | 52.2 |
| | 2 | Biofilm-unextracted | 0.7 | 0.4 | 61.3 |
| | 3 | Biofilm-extracted | 0.6 | 0.2 | 37.3 |
| Cell Lysate | 1 | Planktonic | 0.09 | 0.03 | 30.8 |
| | 3 | Biofilm-extracted | 0.10 | 0.04 | 34.7 |
| | 4 | Biofilm-unextracted | 0.2 | 0.06 | 31.6 |
| Biosurfactant | 1 | Planktonic | 0.12 | 0.05 | 42.2 |
| | 3 | Biofilm-extracted | 0.16 | 0.06 | 36.7 |

Example 2—Isolation and Transformation of Qi611S Gene into *E. coli* BL21

Figure 8:
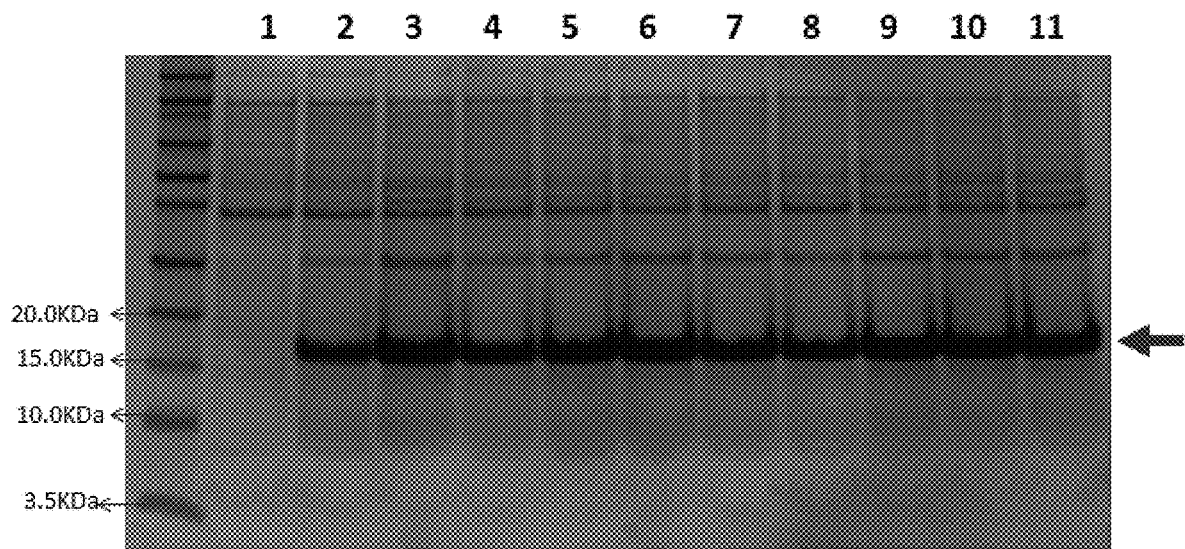
FIG. 8 shows a silver-stained SDS-PAGE gel used to establish the presence of Qi611S synthesized by a recombinant *E. coli* strain. The SDS-PAGE gel was loaded with samples of released protein from the recombinant *E. coli* BL21, which are identified by the bold arrow at the right of the gel. The *E. coli* strain was transformed with the Qi611s gene via the pET-15b expression vector.

A gene encoding Qi611S, Qi611S, can be isolated from *Lactobacillus fermentum* Qi6 and transformed into *E. coli* BL21. As shown in FIG. 8, *E. coli* BL21 is capable of synthesizing a Qi611S protein.

Primers that were used to amplify Qi611S from LF Qi6 can be used to confirm the presence of Qi611S in the *E. coli* cell. The primers used for cloning of Qi611S into the pET-15b vector are listed in Table 3 (see also FIGS. 9-10). These specially-designed primers were obtained from Integrated DNA Technologies (IDT) (Coralville, Iowa).

TABLE 3

Primers used in the cloning of Qi611S for transformation into *E. coli* BL21.

| Primer Name | Primer Sequence (5'-3') |
|---|---|
| Lacto F | CATATGGATAACCGGATTTTCTTCA (SEQ ID NO: 3) |
| Lacto R | GGATCCTTAGAGGTTTTTCTTAATC (SEQ ID NO: 4) |

DNA was isolated and amplified from the Lf Qi6 chromosome that encodes Qi611S using the primers featured in Table 3. The primers enabled the use of two restriction enzymes, NdeI and BamHI, for a restriction enzyme digest of the amplified Qi611S gene and the multiple cloning site of the pET-15b vector.

Once the amplified DNA and the vector are digested using the restriction enzymes, the Qi611S gene is ligated into the vector. The vector can then be transformed into *E. coli* BL21.

The transformed *E. coli* culture is grown overnight at 37° C. and individual colonies are tested for the presence of Qi611S using PCR. Once positive clones are identified, the bacteria can then be grown to identify if Qi611S is successfully encoding synthesis of Qi611S.

The Qi611S protein can be detected by silver staining on SDS-PAGE gel. The SDS-PAGE gel is loaded with released protein samples from *E. coli* BL21 that is expressing Qi611S. The pET-15b vector encodes a polyhistidine-tag, enabling the identification of a synthesized protein without having an antibody specific to the Qi611S. Additionally, the pET-15b encodes the thrombin protease cleavage site (Leu-Val-Pro-Arg-Gly-Ser) to enable removal of the polyhistidine-tag.

Example 3—Antiviral Activity against Porcine Respiratory Coronavirus

Porcine respiratory coronavirus (PRCV) is a single-stranded, negative-sense, RNA virus in the family of Coronaviridae. It was first identified in Belgium in 1984. PRCV is a deletion mutant of the enteric coronavirus transmissible gastroenteritis virus (TGEV) and is also closely related to feline enteric coronavirus and canine coronavirus.

PRCV is spread via aerosol and direct contact between pigs. This usually occurs post-weaning when maternally derived antibody-mediated protection begins to decline. Transmission may also occur in growers/finishers when PRCV-naïve pigs are introduced.

An extract from the biofilm phenotype of LfQi6, designated Qi601S, was tested for activity against PRCV. The tests were conducted in porcine Sertoli (ST) cells. As shown in FIGS. 11-15, 60 hours following co-incubation of a high inoculum dose of the PRCV in porcine Sertoli cells (ST) shows about 100% protection using 5% Qi601S, with no toxicity in cells unchallenged with the PRCV.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

1. Irvine A D, McLean W H, Leung D Y. Filaggrin mutations associated with skin and allergic diseases. N Engl J Med 2011: 365: 1315-1327.
2. Leung D Y, Bieber T. Atopic dermatitis. Lancet 2003: 361: 151-160
3. Malajian D, Guttman-Yassky E. New pathogenic and therapeutic paradigms in atopic dermatitis. Cytokine 2014 Dec. 23: pii: S1043-4666(14)00606-1.
4. Leung D Y, Guttman-Yassky E. Deciphering the complexities of atopic dermatitis: shifting paradigms in treatment approaches. J Allergy Clin Immunol 2014: 134 (4): 769-779.
5. Peng W, Novak N. Pathogenesis of atopic dermatitis. Clin Exp Allerg 2015: 45 (3): 566-574.
6. Boguniewicz M, Leung D Y M. Atopic Dermatitis: a disease of altered skin barrier and immune dysregulation. Immunol Rev 2011 July: 242(1): 233-246.
7. Seguchi T, Chang-Yi C, Kusuda S et al. Decreased expression of filaggrin in atopic dermatitis. Arch Dermatol Res 1996: 288: 442-446.
8. Thyssen J P. Atopic dermatitis, filaggrin mutations and irritant contact dermatitis. Br J Dermatol 2013: 168: 233-234.
9. Howell M D, Kim B E, Gao P et al. Cytokine modulation of atopic dermatitis filaggrin skin expression. J Allergy Clin Immunol 2007: 120: 150-155.
10. Niebuhr M, Heratizadeh A, Wickmann K et al. Intrinsic alterations of pro-inflammatory mediators in unstimulated and TLR-2 stimulated keratinocytes from atopic dermatitis patients. Exp Dermatol 2011: 20: 468-472.
11. Leung D Y, Harbeck R, Bina P et al. Presence of IgE antibodies to staphylococcal exotoxins on the skin of patients with atopic dermatitis. J Clin Invest 1993: 92: 1374-1380.
12. Boguniewicz M. New strategies for dealing with *Staphylococcus aureus* colonization and the emerging methicillin-resistant *Staphylococcus aureus* epidemic in atopic dermatitis. Chem Immunol Allergy 2012: 96: 113-119.
13. Suh L, Coffin S, Leckerman K H et al. Methicillin-resistant *Staphylococcus aureus* colonization in children with atopic dermatitis. Pediatr Dermatol 2008: 25(5): 528-534.
14. Findley K, Grice E A. The Skin microbiome: a focus on pathogens and their association with skin disease. PLoS Pathog 2014: 10(11): e1004436. doi:10.1371/journal.ppat.1004436.
15. Higaki S, Morohashi M, Yamagishi T et al. Comparative study of staphylococci from the skin of atopic dermatitis patients and from healthy subjects. Int J Dermatol 1999: 38: 265-269.
16. van Drongelen V, Haisma E M, Out-Luiting J J et al. Reduced filaggrin expression is accompanied by increased *Staphylococcus aureus* colonization of epidermal skin models. Clin Exp Allergy 2014: 44(12): 1515-1524.
17. Ong P Y, Ohtake T, Brandt C et al. Endogenous antimicrobial peptides and skin infections in atopic dermatitis. N Eng J Med 2002: 347: 1151-1160.
18. Zeeuwen P L, Boekhorst J, van den Bogaard E H et al. Microbiome dynamics of human epidermis following skin barrier disruption. Genome Biol 2012: 13(11): R101.
19. Oh J, Byrd A L, Deming C et al. Biogeography and individuality shape function in the human skin metagenome. Nature 2014: 514(7520): 59-64.
20. Belkaid Y, Segre J A. Dialogue between skin microbiota and immunity. Science 2014: 346(6212): 954.
21. Baviera G, Leoni M C, Capra L et al. Microbiota in healthy skin and in atopic eczema. Biomed Res Int 2014: 436921.
22. Kong H H, Oh J, Deming C et al. Temporal shifts in the skin microbiome associated with disease flares and treatment in children with atopic dermatitis. Genome Res 2012: 22: 850-859.
23. Felten A, Grandry B, Lagrange P H et al. Evaluation of Three Techniques for Detection of Low-Level Methicillin-Resistant *Staphylococcus aureus* (MRSA): a Disk Diffusion Method with Cefoxitin and Moxalactam, the Vitek 2 System, and the MRSA-Screen Latex Agglutination Test. J Clin Microbiol 2002: 40 (8): 2766-2771.

24. Subhadra B, Krier J, Hofstee K et al. Draft whole-genome sequence of *Lactobacillus fermentum* LfQi6, derived from the human microbiome. Genome Announc 2015: 3(3): e00423-15. doi:10.1128/genomeA.00423-15.

25. Conlan S, Mijares L A, NISC Comparative Sequencing Program et al. *Staphylococcus epidermidis* pan-genome sequence analysis reveals diversity of skin commensal and hospital infection-associated isolates. Genome Biol 2012: 13(7): R6

26. Sugimoto S, Iwase T, F. Sato F et al. Cloning, expression and purification of extracellular serine protease Esp, a biofilm-degrading enzyme, from *Staphylococcus epidermidis*. J Appl Microbiol 2011: 111: 1406-1415.

27. Hochstim C J, Choi J Y, Lowe D et al. Biofilm detection with hematoxylin-eosin staining. Arch Otolaryngol Head Neck Surg. 2010: 136(5): 453-456

28. Tuominen V J, Ruotoistenmäki S, Viitanen A et al. ImmunoRatio: a publicly available web application for quantitative image analysis of estrogen receptor (ER), progesterone receptor (PR), and Ki-67. Breast Cancer Res 2010: 12(4): R56.

29. Williams R E, Gibson A G, Aitchison T C et al. Assessment of a contact-plate sampling technique and subsequent quantitative bacterial studies in atopic dermatitis. Br J Dermatol 1990: 123(4): 493-501.

30. Goh C-L, Goh, Wong J S et al. Skin colonization of *Staphylococcus aureus* in atopic dermatitis patients seen at the National Skin Centre, Singapore. Int J Dermatol 1997: 36(9): 653-657.

31. Travers J B, Kozman A, Mousdicas N et al. Infected Atopic Dermatitis Lesions Contain Pharmacologic Amounts of Lipoteichoic Acid. J Allergy Clin Immunol 2010 January: 125(1): 146.

32. Michelsen K S, Aicher A, Mohaupt M et al. The role of toll-like receptors (TLRs) in bacteria-induced maturation of murine dendritic cells (DCS). Peptidoglycan and lipoteichoic acid are inducers of DC maturation and require TLR2. J Biol Chem 2001: 276: 25680-25686

33. Lemjabbar H, Basbaum C. Platelet-activating factor receptor and ADAM10 mediate responses to *Staphylococcus aureus* in epithelial cells. Nature Med 2002: 8: 41-46.

34. Zhang Q, Mousdicas N, Yi Q et al. Staphylococcal lipoteichoic acid inhibits delayed-type hypersensitivity reactions via the platelet-activating factor receptor. J Clin Invest 2005: 115: 2855-2861.

35. Hattar K, Grandel U, Moeller A et al. Lipoteichoic acid (LTA) from *Staphylococcus aureus* stimulates human neutrophil cytokine release by a CD14-dependent, Toll-like-receptor-independent mechanism: Autocrine role of tumor necrosis factor-[alpha] in mediating LTA-induced interleukin-8 generation. Crit Care Med 2006: 34(3): 835-841.

36. Heinemann C, van Hylckama Vlieg J E, Janssen D B et al. Purification and characterization of a surface-binding protein from *Lactobacillus fermentum* RC-14 that inhibits adhesion of *Enterococcus faecalis* 1131. FEMS Microbiol Lett 2000: 190(1): 177-180.

37. de la Fuente-Núñez C, Reffuveille F, Haney E F et al. Broad-spectrum anti-biofilm peptide that targets a cellular stress response. PLoS Pathog 2014: 10(5): e1004152.

38. Haney E F, Mansour S C, Hilchie A L et al. High throughput screening methods for assessing antibiofilm and immunomodulatory activities of synthetic peptides. Peptides 2015: S0196-9781(15): 00073-X.

39. Kim M S, Kim J E, Yoon Y S et al. Improvement of atopic dermatitis-like skin lesions by IL-4 inhibition of P14 protein isolated from *Lactobacillus casei* in NC/Nga mice. Appl Microbiol Biotechnol 2015 [Epub ahead of print]

40. Iwase T, Uehara Y, Shinji H et al. *Staphylococcus epidermidis* Esp inhibits *Staphylococcus aureus* biofilm formation and nasal colonization. Nature 2010: 465 (7296): 346-349. doi: 10.1038/nature09074.

41. Sugimoto S, Iwamoto T, Takada K et al. *Staphylococcus epidermidis* Esp degrades specific proteins associated with *Staphylococcus aureus* biofilm formation and host-pathogen interaction. J Bacteriol 2013: 195(8): 1645-1655.

42. Li D, Lei H, Li Z et al. A novel lipopeptide from skin commensal activates TLR2/CD36-p38 MAPK signaling to increase antibacterial defense against bacterial infection. PLoS One 2013: 8(3): e58288.

43. Lai Y, Cogen A L, Radek K A et al. Activation of TLR2 by a small molecule produced by *Staphylococcus epidermidis* increases antimicrobial defense against bacterial skin infections. J Invest Dermatol 2010: 130(9): 2211-2221.

44. Wang Y, Kuo S, Shu M et al. *Staphylococcus epidermidis* in the human skin microbiome mediates fermentation to inhibit the growth of Propionibacterium acnes: implications of probiotics in acne vulgaris. Appl Microbiol Biotechnol 2014: 98(1): 411-424. doi: 10.1007/s00253 013-5394-8. nature09074.

45. Naik S, Bouladoux N, Wilhelm C et al. Compartmentalized control of skin immunity by resident commensals. Science 2012: 337(6098): 1115-1119. doi: 10.1126/science.1225152.

46. Krishnan A, Nair S A, Pillai M R, Biology of PPAR gamma in cancer: a critical review on existing lacunae. Curr Mol Med 2007: 7(6): 532-40. doi:10.2174/156652407781695765. PMID 17896990.

What is claimed is:

1. A self-decontaminating surface having antiviral properties wherein said surface comprises a composition comprising an isolated bioactive *Lactobacillus fermentum* bacterial strain grown as biofilm; wherein the *Lactobacillus fermentum* strain is *Lactobacillus fermentum* Qi6 having Accession No. PTA-122195, and wherein the surface is cloth, textile, metal, ceramic, or wood.

2. The self-decontaminating surface of claim 1, wherein the virus is an RNA virus.

3. The self-decontaminating surface of claim 2, wherein the virus is a coronavirus.

4. The self-decontaminating surface of claim 2, wherein the coronavirus is SARS-CoV-2.

5. The self-decontaminating surface of claim 2, wherein the coronavirus is SARS-COV.

6. The self-decontaminating surface of claim 2, wherein the coronavirus is MERS-COV.

7. The self-decontaminating surface of claim 1, wherein the surface is cloth.

8. The self-decontaminating surface of claim 1, wherein the surface is textile.

9. The self-decontaminating surface of claim 1, wherein the surface is metal.

10. The self-decontaminating surface of claim 1, wherein the surface is ceramic.

11. The self-decontaminating surface of claim 1, wherein the surface is wood.

12. The self-decontaminating surface of claim 1, wherein the bacterial strain has been grown as a biofilm in culture, and then applied to the surface.

13. The self-decontaminating surface of claim 1, wherein the biofilm on the surface does not comprise any living cells.

* * * * *

SEQUENCE LISTING

```
Sequence total quantity: 6
SEQ ID NO: 1          moltype = AA  length = 74
FEATURE               Location/Qualifiers
source                1..74
                      mol_type = protein
                      organism = Lactobacillus fermentum
SEQUENCE: 1
MDNRIFFNPG DSIANIHDYN EAVRKGQIFK KEQQAGDLVI AKGPDDEEYA IFYANDALPA   60
DHEQSQPYEI KKNL                                                      74

SEQ ID NO: 2          moltype = DNA  length = 225
FEATURE               Location/Qualifiers
source                1..225
```

-continued

```
                         mol_type = genomic DNA
                         organism = Lactobacillus fermentum
SEQUENCE: 2
atggataacc ggattttctt caaccccggc gactcgatcg ccaacatcca cgactacaac    60
gaagccgtcc gcaagggcca aatcttcaaa aaggaacagc aggccggcga cctcgtgatc   120
gctaagggtc ccgatgacga agaatacgcc atcttctacg ccaacgatgc cctgcccgcc   180
gaccacgagc aatcccaacc ctacgagatt aagaaaaacc tctaa                   225

SEQ ID NO: 3           moltype = DNA   length = 25
FEATURE                Location/Qualifiers
source                 1..25
                       mol_type = genomic DNA
                       organism = Lactobacillus fermentum
SEQUENCE: 3
catatggata accggatttt cttca                                          25

SEQ ID NO: 4           moltype = DNA   length = 25
FEATURE                Location/Qualifiers
source                 1..25
                       mol_type = genomic DNA
                       organism = Lactobacillus fermentum
SEQUENCE: 4
ggatccttag aggtttttct taatc                                          25

SEQ ID NO: 5           moltype = DNA   length = 287
FEATURE                Location/Qualifiers
misc_feature           1..287
                       note = primer
source                 1..287
                       mol_type = other DNA
                       organism = synthetic construct
SEQUENCE: 5
agatctcgat cccgcgaaat taatacgact cactataggg gaattgtgag cggataacaa    60
ttcccctcta gaaataattt tgtttaactt taagaaggag atataccatg ggcagcagc    120
atcatcatca tcatcacagc agcggcctgg tgccgcgcgg cagccatatg ctcgaggatc   180
cggctgctaa caaagcccga aaggaagctg agttggctgc tgccaccgct gagcaataac   240
tagcataacc ccttggggcc tctaaacggg tcttgagggg ttttttg                 287

SEQ ID NO: 6           moltype = AA   length = 43
FEATURE                Location/Qualifiers
REGION                 1..43
                       note = primer
source                 1..43
                       mol_type = protein
                       organism = synthetic construct
SEQUENCE: 6
MGSSHHHHHH SSGLVPRGSH MLEDPAANKA RKEAELAAAT AEQ                       43
```